US010694961B2

(12) United States Patent
Dharmakumar et al.

(10) Patent No.: US 10,694,961 B2
(45) Date of Patent: Jun. 30, 2020

(54) ASSESSMENT OF IRON DEPOSITION POST MYOCARDIAL INFARCTION AS A MARKER OF MYOCARDIAL HEMORRHAGE

(75) Inventors: Rohan Dharmakumar, Moorpark, CA (US); Ivan Cokic, Los Angeles, CA (US)

(73) Assignee: CEDARIS-SINAI MEDICAL CENTER, Los Angeles, CA (US)

( * ) Notice: Subject to any disclaimer, the term of this patent is extended or adjusted under 35 U.S.C. 154(b) by 103 days.

(21) Appl. No.: 14/125,307

(22) PCT Filed: Jun. 13, 2012

(86) PCT No.: PCT/US2012/042310
§ 371 (c)(1),
(2), (4) Date: Dec. 10, 2013

(87) PCT Pub. No.: WO2012/174157
PCT Pub. Date: Dec. 20, 2012

(65) Prior Publication Data
US 2014/0113008 A1   Apr. 24, 2014

Related U.S. Application Data

(60) Provisional application No. 61/496,441, filed on Jun. 13, 2011.

(51) Int. Cl.
| *A61B 5/055* | (2006.01) |
| *A61B 5/026* | (2006.01) |
| *A61B 5/00* | (2006.01) |
| *A61B 5/02* | (2006.01) |
| *A61B 5/024* | (2006.01) |
| *A61B 5/0472* | (2006.01) |
| *A61K 45/06* | (2006.01) |
| *A61N 1/362* | (2006.01) |
| *A61N 1/39* | (2006.01) |
| *A61B 5/145* | (2006.01) |
| *A61K 49/06* | (2006.01) |

(52) U.S. Cl.
CPC .......... *A61B 5/0263* (2013.01); *A61B 5/0044* (2013.01); *A61B 5/02042* (2013.01); *A61B 5/02405* (2013.01); *A61B 5/0472* (2013.01); *A61B 5/055* (2013.01); *A61K 45/06* (2013.01); *A61N 1/362* (2013.01); *A61N 1/3956* (2013.01); *A61B 5/14542* (2013.01); *A61B 2576/023* (2013.01); *A61K 49/06* (2013.01)

(58) Field of Classification Search
None
See application file for complete search history.

(56) References Cited

U.S. PATENT DOCUMENTS

| 5,013,718 A * | 5/1991 | Adamson ........... A61K 38/1816 |
| | | 514/5.4 |
| 5,162,313 A | 11/1992 | Kappas et al. |
| 2002/0045573 A1 | 4/2002 | Lai |
| 2006/0051806 A1 | 3/2006 | Rothenberg et al. |
| 2011/0044524 A1 | 2/2011 | Wang et al. |
| 2011/0105575 A1 | 5/2011 | Nick et al. |
| 2016/0183815 A1 | 6/2016 | Dharmakumar et al. |

FOREIGN PATENT DOCUMENTS

WO   2012/174157   12/2012

OTHER PUBLICATIONS

Lewis (Trans. Am. Clin. Climatol Assoc. 1954, 65, 49-76).*
Ellervik et al. (Neurology 2007, 68, 1025-1031).*
Aronow et al. (Arch. Intern. Med. 1969, 123, 433-435).*
Tuomainen et al. (Circulation 1999, 100, 1274-1279).*
Sullivan (Circ. Cardiovasc. Genet. 2009, 2, 653-657).*
Horowitz et al. (Vasc. Med. 1999, 4, 93-99).*
Voogd et al. (J. Clin. Invest. 1992, 90, 2050-2055).*
Klipsein-Grobusch et al. (Am. J. Epidem. 1999, 149, 421-428).*
Lakkisto et al. (E. J. Pharmacol. 2010, 635, 156-164).*
Ghugre et al. (Mag. Reson. Med. 2011, 66, 1129-1141).*
O'Regan et al. (Radiol. 2009, 250, 916-922).*
Anderson et al. (Eur. Heart J. 2001, 22, 2171-2179).*
Bogaert et al. (Eur. Heart J. 2009, 30, 1440-1449).*
Gananne et al. (Eur. Heart J. 2009, 30, 1440-1449).*
Weidler, D. J., "Myocardial Damage and Cardiac Arrhythmias After Intracranial Hemorrhage. A Critical Review.," Stroke;1974; vol. 5, pp. 759-764.
International Search Report for PCT/US2012/042310 dated Aug. 27, 2012, 3 pages.
Written Report for PCT/US2012/042310 dated Aug. 27, 2012, 6 pages.
IPRP for PCT/US2012/042310, 8 pages, Aug. 27, 2012.
Chatterjee et al., Hemodynamic and Metabolic Responses to Vasodilator Therapy in Acute Myocardial Infarction, Circulation, 1973, vol. 48, pp. 1183-1193.
Jugdutt et al., Salvage of Ischemic Myocardium by ibuprofen during Infarction in the Conscious Dog, The American Journal of Cardiology, 1980, vol. 46, pp. 74-82.
Lesnefsky et al., Deferoxamine Pretreatment Reducsed Canine Infarct Size and Oxidavit Injury, The Journal of Pharmacology and Experimental Therapeutics, 1990, vol. 253(3), pp. 1103-1109.
Stenestrand et al., Early Statin Treatment Following Acute Myocardial Infarction and 1-Year Survival, JAMA, 2001, vol. 285(4), pp. 430-436.
Goldfarb et al., Myocardial Fat Deposition after Left Ventricular Myocardial Infarction: Assessment by Using MR Water-Fat Seperation Imaging, Radiology, 2009, vol. 253(1), pp. 65-73.

(Continued)

Primary Examiner — Michael G. Hartley
Assistant Examiner — Melissa J Perreira
(74) Attorney, Agent, or Firm — Nixon Peabody LLP

(57) ABSTRACT

The invention is directed to methods for diagnosing reperfusion/non-reperfusion hemorrhage and predicting cardiac arrhythmias and sudden cardiac death in subjects comprising using imaging techniques to detect regional iron oxide deposition. The invention also provides treatment methods for subject at increased risk of sudden cardiac death.

21 Claims, 14 Drawing Sheets

(56) References Cited

OTHER PUBLICATIONS

Ono et al., Nicorandil Improves Cardiac Function and Clinical Outcome in Patients with acute Myocardial Infarction Undergoing Primary Precutaneous Coronary Internvention: Role of Inhibitory Effect on Reactive Oxygen Species Formation, American Heart Journal, 2004, vol. 148(4), pp. 1-7.

* cited by examiner

ASSESSMENT OF IRON DEPOSITION POST MYOCARDIAL INFARCTION AS A MARKER OF MYOCARDIAL HEMORRHAGE

CROSS-REFERENCE TO RELATED APPLICATIONS

This application is the National Phase of International Application PCT/US2012/042310, filed Jun. 13, 2012, which designated the U.S. and that International Application was published under PCT Article 21(2) in English. The present application also claims the benefit of the filing date of U.S. Provisional Application No. 61/496,441 filed Jun. 13, 2011, the contents of each of which are herein incorporated by reference.

STATEMENT REGARDING FEDERALLY SPONSORED RESEARCH OR DEVELOPMENT

This invention was made with government support under Grant No. HL091989 awarded by the National Institutes of Health. The government has certain rights in the invention.

FIELD OF INVENTION

The invention is directed to methods for diagnosing reperfusion and non-reperfusion hemorrhage, predicting cardiac arrhythmias, sudden cardiac death, and adverse remodeling in subjects post myocardial infarction. The invention also provides treatment methods for subjects at increased risk of sudden cardiac death and heart failure.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Significant narrowing of epicardial coronary arteries due to atherosclerotic disease or acute embolic obstruction can impede blood flow and oxygen to the myocardium resulting in acute myocardial infarction (AMI). Reperfusion therapy is the standard of care for restoring blood flow to the ischemic myocardial tissue. However, reperfusion therapies are also associated with post-infarct complications that are often associated with fatal heart failure. Most heart failures have an origin in ischemic heart disease and fatalities from it are largely related to Sudden Cardiac Death (SCD). In majority of cases, SCD is triggered by the onset of cardiac arrhythmias, an abnormally rapid heart rate originating in the ventricle and/or atria. If undetected and untreated, this can degenerate into asystole leading to hemodynamic impairment causing death.

Although there are diagnostic and therapeutic strategies for managing and treating ischemic heart disease, these strategies have limited value for distinguishing individual patients at risk for arrhythmias and SCD. The symptoms of ventricular arrhythmias (VA) are palpitations, chest pain, presyncope and syncope. In post-myocardial infarction patients or patients with VA symptoms, a 12-lead ECG, Holter monitoring and loop recorders are used to detect cardiac arrhythmias. However, there are no diagnostic strategies for predicting SCD before the onset of symptoms accompanying cardiac arrhythmias.

The spectrum of therapies also has limited benefits. Anti-arrhythmic drugs are frequently prescribed to suppress potential cardiac arrhythmia triggers, but most patients experience serious side effects and more than 40% of patients experience sustained VA recurrence within two years of starting the therapy. Moreover, a majority of anti-arrhythmia medications have pro-arrhythmic potential in patients with structural heart disease, thus, the current ACC (American College of Cardiology) guidelines recommend that antiarrhythmic drugs other than βblockers should not be used to treat VA unless the patient is protected by an implantable cardioverter-defibrillator (ICD). Cardioversion by shock therapy can be achieved by external electrical defibrillation or internally via an ICD that continuously monitors for and detects episodes of VA. However, ICD therapy is a non-curative approach for patients with VA. It is associated with significantly decreased quality of life associated with VA symptoms and distress of anticipating ICD activation. Radio frequency ablation offers a potential curative therapy, however the major challenge is the identification of the location of the VA substrate.

Reperfusion hemorrhage is a common consequence of re-establishing epicardial blood flow into severely ischemic myocardium. To date, the long-term effects of hemorrhagic infarcts on electrical conduction in the heart have not been studied. The inventor demonstrates that reperfusion hemorrhage leads to deposition of iron particulates within chronic infarcts and examines their role in mediating cardiac arrhythmias (abnormal and rapid beating of heart originating in the ventricle).

SUMMARY OF THE INVENTION

The invention provides a method for diagnosing reperfusion and non-reperfusion hemorrhage in a subject in need thereof comprising obtaining MRI images of the subject's heart, detecting regional iron oxide deposition in the heart, and diagnosing presence or absence of hemorrhage in the subject, wherein presence of iron oxide deposition in regions of the heart is indicative of hemorrhage in the subject, thereby diagnosing hemorrhage in the subject.

The invention is also directed to a method for predicting cardiac arrhythmias in a subject in need thereof comprising diagnosing hemorrhage in the subject by the method described above, wherein presence of hemorrhage is indicative of increased likelihood of cardiac arrhythmias in the subject, thereby predicting cardiac arrhythmias in the subject.

The invention is further directed to a method for predicting sudden cardiac death in a subject in need thereof comprising predicting cardiac arrhythmias by the method described above, wherein increased likelihood of cardiac arrhythmias is indicative of increased likelihood of sudden cardiac death in the subject, thereby predicting sudden cardiac death in the subject.

The invention also provides a method for treating a subject at an increased risk of sudden cardiac death or heart failure associated with regional iron deposition in the heart comprising administering to the subject an effective amount of a chelating agent, so as to treating the subject at an increased risk of sudden cardiac death associated with regional iron deposition in the heart.

The invention further provides a method for determining the prognosis after a myocardial infarction in a subject in need thereof comprising diagnosing reperfusion hemorrhage in the subject by the method described above, wherein the presence of reperfusion and non-reperfusion hemorrhage in the subject is indicative of a poor prognosis, thereby determining the prognosis of a myocardial infarction in the subject.

DETAILED DESCRIPTION OF THE INVENTION

Figure 1:
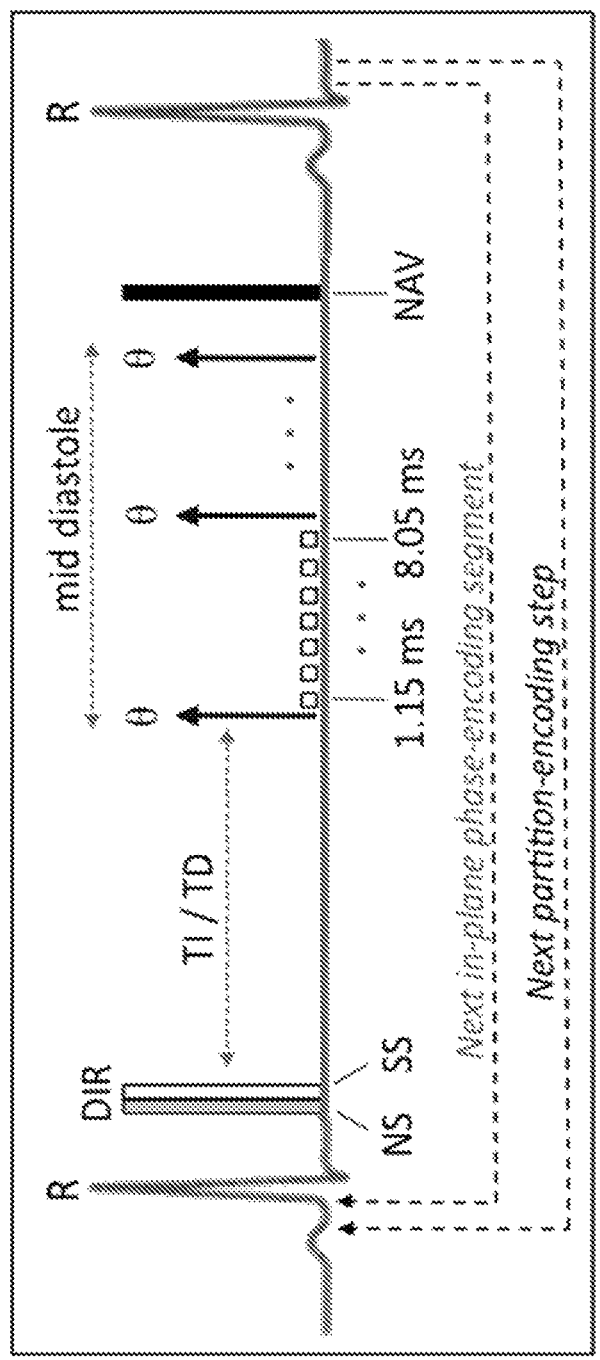
FIG. 1 depicts the timing diagram for navigator-gated, ECG-triggered segmented, dark-blood prepared 3D multi gradient-echo T2* mapping sequence. Double Inversion block (DIR) is (non-selective (NS) and slice-selective (SS) inversion pulses; TI is the inversion time to null blood; θ is the flip angle; and NAV is the navigator pulse for respiratory gating. DIR is applied during late diastole with a trigger delay (also the TI time) during which the blood in the left-ventricle (inverted by the SS pulse) is replaced with fresh blood prior to data acquisition (mid diastole).

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Treatment" and "treating," as used herein refer to both therapeutic treatment and prophylactic or preventative measures, wherein the object is to prevent or slow down (lessen) the targeted pathologic condition, prevent the pathologic condition, pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Mechanical abnormalities" as used herein refers to deviations in cardiac contractions that lead to changes in mechanical deformations that mediate potential changes in standard volumetric indices. Regional abnormalities in cardiac contraction leading to alterations in volumetric indices including but not limited to ejection fraction (EF), blood pressure, cardiac output (CO), and/or left ventricle end diastolic volume (LVEDV) in the heart due to iron deposition post myocardial infarction. Poor myocardial contraction can also lead to blood stasis (i.e. clot/thrombus formation), which can subsequently become a systemic embolus/emboli that lead to stroke, secondary myocardial infarction, or cause other vascular obstructions.

"Electrical abnormalities" as used herein refer to deviation in heart rhythm and heart rate. In particular, the surface ECG and endo- and/or epi-cardial electrograms that identify changes in QRS duration, QT duration/dispersion, heart-rate variability, Q-waves, T-waves, effective refractory period (ERP), action potential duration, isolated late potentials, or combinations thereof may be used.

"Hemorrhage" as used herein refers to pooling or extravasation of blood into the interstitial space The invention is directed towards developing a non-invasive image-guided approach, based on Magnetic Resonance Imaging (MRI), for predicting cardiac arrhythmias that cause sudden cardiac death. While not wishing to be bound by any particular theory, the inventors hypothesize that reperfusion hemorrhaging leads to localized depositions of iron oxide within the myocardium, which can be characterized by MRI. These iron particulates may act as substrates for cardiac arrhythmias mediating sudden cardiac death. The inventors have also show that hemorrhage of the myocardium is not only limited to reperfusion but is also associated with non-reperfused myocardial infarction and that such infarctions also lead to gross deposition of iron-oxide. Since iron oxide induces changes in electrical properties of myocardium, both non-reperfused and reperfused MIs with iron deposition are prone to a higher degree of risk of cardiac arrhythmias.

Free-Breathing 3D T2* Maps at 3 T for Characterizing Iron Depositions in the Heart Breath-held, ECG-triggered, 2D T2* mapping at 1.5 T is the current standard for identifying iron overload in the heart. However, this approach has a number of limitations for the inventors' application: (i) the inventor's early studies and the literature suggest that, in the setting of large infarcts, breath holding may trigger arrhythmias, (ii) repetitive breath-held image acquisitions have led to fatal arrhythmias in canines with hemorrhage, and (iii) non-fatal arrhythmias demand undesirably long breath holding times. Partial volume effects in the through-plane direction can significantly reduce the conspicuity of the regions with an iron overload.

Bright blood T2* maps are prone to significant image artifacts (ghosts and smearing), particularly when echo times (TE) are long. At 1.5 Tesla (T), the sensitivity for visualizing smaller iron depositions can be limited and require the use of longer TEs in spite first-order flow compensation at every TE. Doubling the field strength is known to increase the image contrast for detecting iron particulates by a factor of 4, which in turn implies that significantly shorter TEs may be used to generate T2* maps. Flow compensation at shorter TEs and dark-blood imaging may be ideal for overcoming these artifacts.

The current approach also has limited signal-to-noise (S/N) characteristics. 3D mGRE acquisitions, particularly when performed at 3.0 T, can increase the S/N and permit the use of image acceleration strategies to reduce scan time without compromising S/N. The herein proposed dark-blood T2* MRI may provide greater patient comfort/safety, substantially improved image quality and sensitivity for detecting localized myocardial iron deposits.

Iron Deposition in Chronic Infarcts Following Reperfusion and Non-Reperfusion

Until recently, non-invasive imaging methods for detecting reperfusion and non-reperfusion in vivo were not available. Therefore, studies of reperfusion and non-reperfusion relied solely on autopsy data, were primarily observational descriptions, and were limited in size. Although T2*-based detection of reperfusion is gaining recognition, the fate of reperfusion hemorrhage and its relation to an aging (chronic) infarction has not been previously studied. The inventor herein provides evidence (both imaging and histology) to suggest that reperfusion and non-reperfusion hemorrhage leads to regional iron overloading in the heart and may have a role in the progression of heart failure.

Iron Deposits within Chronic Infarcts Mediating Fatal Cardiac Arrhythmia

Cardiac arrhythmias are common among patients with reperfused and non-reperfused infarctions, and if untreated and undetected, they can cause sudden cardiac death. Current understanding is that the infarct territories enable re-entry currents leading to ventricular tachycardia (VT) or VF. However, it is also known that not all infarct territories can mediate cardiac arrhythmias. In fact, the true substrate(s) that catalyze cardiac arrhythmia are not fully understood. The inventors propose that iron deposition within the chronic infarcts (cMI) may be an important substrate for altering the electrical conductivity in the heart. The inventor hypothesizes that iron deposits from hemorrhagic infarcts, hemosiderin (highest conductive compound found in living organisms can alter the tissue capacitance and thereby serve as a source of potential (voltage) sinks. As the conduction potential is drained from the depolarizing current, regional conduction abnormalities culminate in mechanical dysynchrony, which facilitate hemodynamic impairment causing death. The inventors' show that cMI with iron overload have significantly greater electrical capacitance than healthy (remote). Identification of iron particulates as a critical substrate for cardiac arrhythmia on the basis of noninvasive imaging is likely to be a significant finding in the overall understanding of SCD in patients with a history of cMI.

Reducing the Risk of Fatal Ventricular Arrhythmias or Adverse Ventricular Remodeling Via Drug Therapy Chronic, localized, iron overloading is a feature of hemorrhagic stroke. Such iron overload has been shown to catalyze free-radical reactions that lead to significant tissue damage. The benefits of iron chelation therapies in this setting are well recognized. Additionally, chelation therapies in the heart for thalassemia (ferritin cardiomyopathy) have also shown to be highly beneficial. These studies suggest that the use of clinically approved iron chelators, such as Deferoxamine, may also allow for the removal of iron deposits from reperfusion and non-reperfusion hemorrhage in the heart. To date, the use of chelators for removing myocardial iron deposits from infarcted territories has not been studied. The demonstration that iron chelators may be used to reduce the risk of cardiac arrhythmia in patients with a history of chronic infarction may prove to be an important medical treatment for infarct patients with a risk of SCD.

In addition to chelation therapies to remove iron oxide deposits, carbon monoxide therapies, and other haem-oxygenase regulating drugs may also be used to prevent deposition of iron. These additional drug therapies can be used alone or in conjunction with chelation therapies to augment the reduction of iron in myocardial tissue. In some embodiments, subjects with iron oxide deposits are implanted with an implantable cardioverter-defibrillator (ICD) or a pacemaker.

Diagnostic and Treatment Methods of the Invention

The invention is directed to methods for diagnosing reperfusion and/or non-reperfusion hemorrhage in a subject in need thereof. The method comprises obtaining images of the subject's heart, detecting regional iron oxide deposits in the heart, and diagnosing presence or absence of reperfusion and/or non-reperfusion hemorrhage in the subject. The presence of iron oxide deposits in regions of the heart is indicative of reperfusion and/or non-reperfusion hemorrhage in the subject. Alternatively, an increase in the iron oxide deposition in regions of the subject's heart compared to the control subject is indicative of reperfusion and/or non-reperfusion hemorrhage in the subject. In some embodiments, the method further comprises measuring blood and/or serum levels of any one or more of hepcidin, carbon monoxide, bilirubin, unbound iron binding capacity (UIBC), Fe bound to transferrin, ferritin, heme (heam) oxygenase, biliverdin or a combination thereof in the subject. An increase in any one or more of hepcidin, biliverdin, bilirubin, carbon monoxide, heme (haem) oxygenase, Fe bound to transferrin, ferritin and/or a decrease in UIBC is indicative of hemorrhagic infarction in the subject (Okuhara et al., Change in bilirubin level following acute myocardial infarction is an index for heme oxygenase activation *South Med J.* 2010 September; 103(9):876-81; *Peptides* 2010 September; 31(9):1786-90. Epub 2010 May 27). In one embodiment, the subject is a myocardial infarction patient that has undergone reperfusion. In another embodiment, the subject is a myocardial infarction patient that has not undergone reperfusion.

The invention also provides methods for diagnosing myocardial hemorrhage in subjects that are treated with anti-platelet drugs and/or anticoagulant drugs. In some embodiments, the side-effects of antiplatelets and/or anticoagulants include subjects later developing hemorrhagic infarctions resulting in increased risk of cardiac arrhythmias and/or heart failure. Accordingly, the method comprises obtaining images of the subject's heart, detecting regional iron oxide deposits in the heart, and diagnosing presence or absence of myocardial hemorrhage associated wherein the subject is or was administered antiplatelet drugs and/or anticoagulant drugs. The presence of iron oxide deposits in regions of the heart is indicative of myocardial hemorrhaging in the subject. Alternatively, an increase in the iron oxide deposition in regions of the subject's heart compared to the control subject is indicative of myocardial hemorrhaging in the subject. In some embodiments, the method further comprises measuring blood and/or serum levels of any one or more of hepcidin, carbon monoxide, bilirubin, unbound iron binding capacity (UIBC), Fe bound to transferrin, ferritin, heme (heam) oxygenase, biliverdin or a combination thereof in the subject. An increase in any one or more of hepcidin, biliverdin, bilirubin, carbon monoxide, heme (haem) oxygenase, Fe bound to transferrin, ferritin and/or a decrease in UIBC is indicative of hemorrhagic infarction in the subject, wherein the subject is or was administered antiplatelet drugs and/or anticoagulant drugs. In some embodiments, myocardial hemorrhaging in subjects that were or are administered antiplatelet drugs and/or anticoagulant drugs, is indicative of increased risk of cardiac arrhythmias and/or heart failure.

The invention also provides methods for predicting cardiac arrhythmias in a subject in need thereof comprising. The method for predicting cardiac arrhythmias includes diagnosing reperfusion and/or non-reperfusion hemorrhage in the subject comprising obtaining images of the subject's heart, detecting regional iron oxide deposition in the heart, and diagnosing presence or absence of reperfusion and/or non-reperfusion hemorrhage in the subject. The presence of iron oxide deposits in regions of the subject's heart is indicative of reperfusion and/or non-reperfusion hemorrhage in the subject. The presence of reperfusion and/or non-reperfusion hemorrhage in the subject is indicative of increased likelihood of cardiac arrhythmias. In some embodiments, the method further comprises measuring blood and/or serum levels of any one or more of hepcidin, carbon monoxide, bilirubin, unbound iron binding capacity (UIBC), Fe bound to transferrin, ferritin, heme (heam) oxygenase, biliverdin or a combination thereof in the subject. An increase in any one or more of hepcidin, biliverdin, bilirubin, carbon monoxide, heme (haem) oxygenase, Fe bound to transferrin, ferritin and/or a decrease in UIBC is indicative of hemorrhagic infarction and increased likelihood of cardiac arrhythmias in the subject. In one embodiment, the subject is a myocardial infarction patient that has undergone reperfusion. In another embodiment, the subject is a myocardial infarction patient that has not undergone reperfusion.

The invention also provides methods for predicting sudden cardiac death in a subject in need thereof. The method comprises diagnosing reperfusion and/or non-reperfusion hemorrhage and/or detecting regional iron oxide deposits in the subject's heart by the methods described above. In an embodiment, the methods comprise obtaining images of the subject's heart, detecting regional iron oxide deposits in the heart, and diagnosing presence or absence of reperfusion and/or non-reperfusion hemorrhage in the subject. The presence of iron oxide deposits in regions of the subject's heart is indicative of reperfusion and/or non-reperfusion hemorrhage in the subject and therefore is indicative of increased likelihood of sudden cardiac death or cardiac arrhythmias in the subject. In some embodiments, the method further comprises measuring blood and/or serum levels of any one or more of hepcidin, carbon monoxide, bilirubin, unbound iron binding capacity (UIBC), Fe bound to transferrin, ferritin, heme (heam) oxygenase, biliverdin or a combination thereof in the subject. An increase in any one or more of hepcidin, biliverdin, bilirubin, carbon monoxide, heme (haem) oxygenase, Fe bound to transferrin, ferritin and/or a decrease in UIBC is indicative of hemorrhagic infarction, increased likelihood of sudden cardiac death and/or cardiac arrhythmias in the subject. In one embodiment, the subject is a myocardial infarction patient that has undergone reperfusion. In another embodiment, the subject is a myocardial infarction patient that has not undergone reperfusion.

Also provided is a method for determining the prognosis after a myocardial infarction in a subject in need thereof. The method comprises diagnosing reperfusion/non-reperfusion hemorrhage and/or regional iron oxide deposits in the subject's heart by the methods described above. In one embodiment, the presence of reperfusion/non-reperfusion hemorrhage and/or regional iron oxide deposit in the subject is indicative of a poor prognosis. In another embodiment, increased reperfusion/non-reperfusion hemorrhage and/or regional iron oxide deposit in the subject compared to the control subject is indicative of poor prognosis. In some embodiments, the method further comprises measuring blood and/or serum levels of any one or more of hepcidin, carbon monoxide, bilirubin, unbound iron binding capacity (UIBC), Fe bound to transferrin, ferritin, heme (heam) oxygenase, biliverdin or a combination thereof in the subject. An increase in any one or more of hepcidin, biliverdin, bilirubin, carbon monoxide, heme (haem) oxygenase, Fe bound to transferrin, ferritin and/or a decrease in UIBC is indicative of hemorrhagic infarction and poor prognosis in the subject. In one embodiment, the subject is a myocardial infarction patient that has undergone reperfusion. In another embodiment, the subject is a myocardial infarction patient that has not undergone reperfusion.

Additionally, the invention provides methods for treating a subject at an increased risk of sudden cardiac death. The method comprises administering an effective amount of a chelating agent to the subject so as to treat the subject at an increased risk of sudden cardiac death. In an embodiment, an increased risk of sudden cardiac death is associated with one or more regional iron deposits in the heart. In an embodiment, carbon monoxide therapies and other haem-oxygenase regulating drugs may also be used to treat or prevent deposition of iron oxide. Carbon monoxide therapies and haem-oxygenase regulating drugs may be used alone or in conjunction with chelation therapies to augment the prevention/reduction of iron in myocardial tissue. In some embodiments, subjects with iron oxide deposits are implanted with an implantable cardioverter-defibrillator (ICD) or a pacemaker. In one embodiment, the subject is a myocardial infarction patient that has undergone reperfusion. In another embodiment, the subject is a myocardial infarction patient that has not undergone reperfusion.

The invention further provides a method for treating a subject with localized deposits of iron oxide in myocardial tissue. The method includes obtaining MRI images of the subject's heart, detecting localized iron oxide deposition in the heart, providing a composition comprising a chelating agent and administering an effective amount of the composition to the subject so as to treat a subject with localized deposition of iron in the myocardial tissue. In some embodiments, the localized deposition of iron in the myocardial tissue results in cardiac arrhythmia. In some embodiments, cardiac arrhythmia is atrial fibrillation and ventricular arrhythmia. In various embodiments, atrial arrhythmia includes but is not limited to atrial fibrillation, atrial flutter and/or a combination thereof and ventricular arrhythmia includes but is not limited to ventricular tachycardia, ventricular fibrillation, bundle-branch block, A-V block, and/or a combination thereof. In an embodiment, carbon monoxide therapies and other haem-oxygenase regulating drugs may also be used to remove iron oxide deposits. Carbon monoxide therapies and haem-oxygenase regulating drugs may be used alone or in conjunction with chelation therapies to augment the prevention/reduction of iron in myocardial tissue. In some embodiments, subjects with iron oxide deposits are implanted with an implantable cardioverter-defibrillator (ICD) or a pacemaker. In one embodiment, the subject is a myocardial infarction patient that has undergone reperfusion. In another embodiment, the subject is a myocardial infarction patient that has not undergone reperfusion.

The invention further provides methods for treating a subject with electrical conduction abnormalities and/or mechanical abnormalities in the myocardium. In an embodiment, the electrical conduction abnormalities and/or mechanical abnormalities are due to localized deposits of iron oxide in the myocardium. The treatment method includes obtaining MRI images of the subject's heart, detecting localized iron oxide deposition in the heart, providing a composition comprising a chelating agent and administering an effective amount of the composition to the subject so as to treat a subject with electrical conduction abnormalities and/or mechanical abnormalities in the myocardium. In an embodiment, carbon monoxide therapies and other haem-oxygenase regulating drugs may also be used to remove iron oxide deposits. Carbon monoxide therapies and haem-oxygenase regulating drugs may be used alone or in conjunction with chelation therapies to augment the prevention/reduction of iron in myocardial tissue. In some embodiments, subjects with iron oxide deposits are implanted with an implantable cardioverter-defibrillator (ICD) or a pacemaker. In one embodiment, the subject is a myocardial infarction patient that has undergone reperfusion. In another embodiment, the subject is a myocardial infarction patient that has not undergone reperfusion.

The invention further provides a method for reducing myocardial inflammation in subjects in need thereof. The method includes obtaining MRI images of the subject's heart, detecting regional iron oxide deposits in the heart, wherein presence of iron oxide deposits is indicative of increased myocardial inflammation; and administering an effective amount of a composition comprising a chelating agent so as to reduce myocardial inflammation in the subject. In an embodiment, the subject has undergone one or more hemorrhagic infarctions resulting in myocardial inflammation. In an embodiment, carbon monoxide therapies and other haem-oxygenase regulating drugs may also be used to remove iron oxide deposits. Carbon monoxide therapies and haem-oxygenase regulating drugs may be used alone or in conjunction with chelation therapies to augment the prevention/reduction of iron in myocardial tissue. In some embodiments, subjects with iron oxide deposits are implanted with an implantable cardioverter-defibrillator (ICD) or a pacemaker. In one embodiment, the subject is a myocardial infarction patient that has undergone reperfusion. In another embodiment, the subject is a myocardial infarction patient that has not undergone reperfusion.

The invention also provides a method for reducing adverse remodeling of the heart in subject in need thereof. The method includes obtaining MRI images of the subject's heart, detecting regional iron oxide deposits in the heart, wherein presence of iron oxide deposits is indicative of increased myocardial inflammation; and administering an effective amount of a composition comprising a chelating agent so as to reduce myocardial inflammation in the subject and thereby reducing the adverse remodeling of the heart. In an embodiment, the subject has undergone one or more hemorrhagic infarctions resulting in myocardial inflammation. In an embodiment, carbon monoxide therapies and other haem-oxygenase regulating drugs may also be used to prevent iron deposition. Carbon monoxide therapies and haem-oxygenase regulating drugs may be used alone or in conjunction with chelation therapies to augment the prevention/reduction of iron in myocardial tissue. In one embodiment, the subject is a myocardial infarction patient that has undergone reperfusion. In another embodiment, the subject is a myocardial infarction patient that has not undergone reperfusion.

The invention also provides a method for predicting cardiac arrhythmias in a subject in need thereof. The method includes obtaining MRI images of the subject's heart and detecting regional iron oxide deposits in the heart. In an embodiment, the subject has not undergone a myocardial infarction. The presence of iron oxide deposits in one or more regions of the heart is indicative of increased likelihood of cardiac arrhythmia in the subject, so as to predict cardiac arrhythmia in the subject. In one embodiment, the subject is a myocardial infarction patient that has undergone reperfusion. In another embodiment, the subject is a myocardial infarction patient that has not undergone reperfusion.

In various embodiments of the invention, the subject is any one or more of myocardial infarction patient, a patient with ischemic heart disease, a patient with chronic iron deposition in the heart or a combination thereof. In some embodiments, the subject is a myocardial infarction patient whose treatment is initiated at least 2 hours, at least 3 hours, at least 4 hours, at least 5 hours or at least 6 hours after the onset of symptoms of myocardial infarction. In a further embodiment, the symptoms of onset of myocardial infarction are any one or more of chest pain, elevated ST segment in an electrocardiogram (ECG), elevated troponin levels in the blood or a combination thereof.

In some embodiments, the images for the methods of the invention are obtained using Magnetic Resonance Imaging (MRI) or Computed Tomography (CT). In an embodiment, the images for the methods of the invention are obtained using MRI.

In some embodiments, images may be obtained 4-24 hours post-reperfused or non-reperfused MI, 1-5 days post reperfused or non-reperfused MI, 5-10 days post reperfused or non-reperfused MI, 10-15 days post reperfused or non-reperfused MI, 15-20 days post reperfused or non-reperfused MI, 20-25 days post reperfused or non-reperfused MI and/or 25-30 days post reperfused or non-reperfused MI. Images may also be acquired in the chronic period following infarction, several months post MI for detection of chronic iron deposition.

In a further embodiment, iron levels at or above 0.04 mg/g of tissue within infarcted myocardium is indicative of hemorrhagic infarction in the subject.

In one embodiment, the chelating agent may be any one or more of Deferoxamine, Deferasirox, Deferiprone or a combination thereof. In another embodiment, the chelating agents (for example Deferoxamine, Deferasirox, Deferiprone) may be used at a dose of any one or more of 100-200 mg/day, 200-300 mg/day, 300-400 mg/day, 400-500 mg/day, 500-600 mg/day, 600-700 mg/day, 700-800 mg/day, 800-

900 mg/day, 900-100 mg/day or a combination thereof. The chelating agent may be administered intramuscularly (IM). If more than one chelating agent is used, each chelating agent may be administered concurrently or sequentially. A person of ordinary skill in the art would know the optimum chelating agent that may be used for iron oxide removal and the optimum dosage of the one or more chelating agents that may be used for iron oxide removal.

In some embodiments, carbon monoxide therapies and other haem-oxygenase regulating drugs may also be used to prevent iron deposition in myocardium (Motterlini R, Otterbein LE, Therapeutic Potential of Carbon Monoxide, *Nature*, 2010 September; 9(9):728-43; Pamplona et al., Heme oxygenase-1 and carbon monoxide suppress the pathogenesis of experimental cerebral malaria, 2007 *Nature Medicine* Vol 13, 703-710). Carbon monoxide therapies and haem-oxygenase regulating drugs may be used alone or in conjunction with chelation therapies to augment the prevention/reduction of iron in myocardial tissue. In an embodiment, carbon monoxide therapies and other haem-oxygenase regulating drugs may also be used to remove iron oxide deposits. Carbon monoxide therapies and haem-oxygenase regulating drugs may be used alone or in conjunction with chelation therapies to augment the prevention/reduction of iron in myocardial tissue. In some embodiments, subjects with iron oxide deposits are implanted with an implantable cardioverter-defibrillator (ICD) or a pacemaker.

Carbon monoxide (CO) and haem-oxygenase regulating drugs may be administered via inhalational, intraperitoneally (i.p), intravenously (i.v), orally (p.o), and/or topically. In some embodiments, the dosage of carbon monoxide is such that the carboxyhemoglobin levels do not exceed 20%. The amount of CO administered may be any one or more of 0.1-0.5 ppm, 0.5-5 ppm, 5-50 ppm, 50-100 ppm, 100-200 ppm, 200-300 ppm 300-400 ppm, 0.1-400 ppm or a combination thereof.

In an additional embodiment, the subject is any one or more of human, monkey, ape, dog, cat, cow, horse, goat, pig, rabbit, mouse and rat.

One of the major complications associated with myocardial infarctions is post-infarct remodeling of the heart, which in time culminates in heart failure. The inventor hypothesizes that one of the key factors that drive an infarcted heart into heart failure is the presentation of iron from biodegradation of intramyocardial hemorrhage. Elevated tissue deposition of iron is expected to increase oxidative stress to the myocardium resulting in increased tissue necrosis in the acute phase of the infarction. In response, the remodeling of the heart in the post-infarct period is accelerated compared to infarctions that are non-hemorrhagic.

Since MRI can be used to determine whether reperfusion therapy or no reperfusion has led to hemorrhage, the imaging information can be used to evaluate improved reperfusion strategies that pre-emptively limit hemorrhage and/or aid in chelation (or other medical) therapies aimed at preventing the iron from hemorrhagic infarction in the post-reperfusion phase.

Advantages of the Invention

This invention provides a method for classifying an infarction (both reperfused and non-reperfused types) to be hemorrhagic or non-hemorrhagic based on MRI in order to provide therapeutic interventions to prevent iron deposition in the chronic period of infarction. In addition it also provides a means to verify whether the therapeutic intervention was effective in preventing hemorrhagic infarction, subsequent iron deposition, or serial imaging to determine the rate of clearance of iron deposition.

EXAMPLES

Example 1

Experimental Methods
Surgical Procedure

Figure 10:
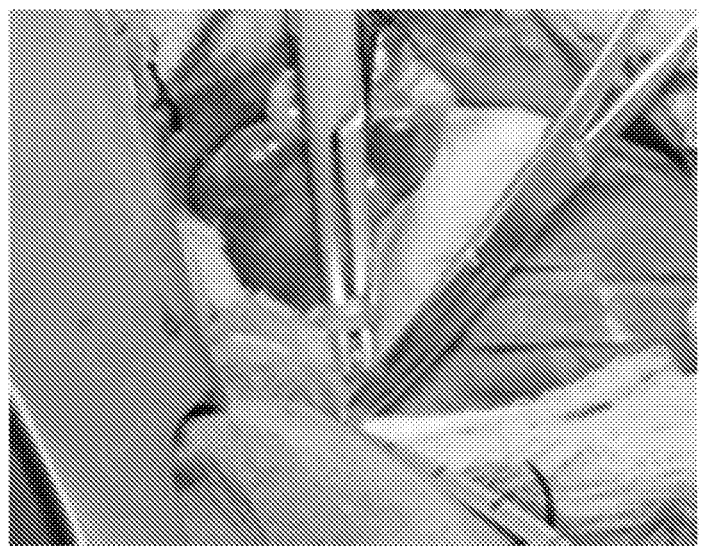
FIG. 10 depicts the isolation of left anterior descending (LAD) artery for the placement of hydraulic occluder.

Canines (n=23, 20-25 kg) were enrolled and studied according to the protocols approved by the Institutional Animal Care and Use Committee. Each dog was given an intramuscular injection of the pre-anesthetic tranquilizer Innovar (0.4 mg/ml of fentanyl and 20 mg/ml of droperidol) at a dose of 1 ml/25-50 kg of body weight. Subsequently, the dog was anesthetized with an intravenous injection of Propofol (5.0-7.5 mg/kg), endotracheally intubated and maintained on gas anesthesia (2.0-2.5% isoflurane with 100% oxygen). Animals were artificially ventilated at 1-2 L/min with the respiration rate being continuously adjusted to maintain partial pressure of $CO_2$ in blood ($PaCO_2$) between 30 and 35 mmHg. Left lateral thoracotomy was performed at the fourth intercostal space, and the exposed heart was suspended in a pericardial cradle (FIG. 10). Aortic and left atrial catheters were inserted and secured for invasive blood pressure monitoring and drug delivery. A portion of the proximal left anterior descending artery (LAD) was isolated and a hydraulic occluder was looped around the vessel 1.0-1.5 cm distal to the bifurcation of left main coronary artery. A Doppler ultrasound flow probe (Crystal Biotech, Northborough, Mass.) was circumferentially secured 2.0-2.5 cm downstream from the occluder to verify the fidelity of occlusion. Systemic $O_2$ saturation, $PaCO_2$, body temperature, blood pressure, respiration rate, heart rhythm and rate were continuously monitored throughout the surgery. The chest was closed and the dog was allowed to recover for 7 days prior to I/R injury.

Inducing Ischemia-Reperfusion Injury

On day 7 post-surgery, each dog was anesthetized and reversible LAD stenosis was induced by gently forcing saline through the open end of the occluder tubing using a micro-push syringe (250 µl GASTIGHT syringe, Hamilton Company, Reno, Nev.) resulting in the constriction of LAD. The extent of LAD occlusion was continuously monitored by Doppler flow velocities. After achieving complete LAD occlusion, the ballooned tubing was clamped and held for 3 hours. At the end of 3 hours of ischemia, reperfusion was established by releasing the clamp and completely drawing out the saline from the tubing. Vital parameters, similar to those described earlier for the surgical procedure, were continuously monitored. To minimize fatal ventricular arrhythmias from I/R injury, all dogs were pre-treated with Amiodarone (200 mg/day, TEVA Pharmaceuticals USA, Sellersville, Pa.) for 2 weeks prior to I/R injury. Arrhythmias occurring during the ischemia and reperfusion were controlled by intravenous injection of 1-2 ml lidocaine (20 mg/ml) as needed.

Experimental Groups

All animals underwent proton Magnetic Resonance Imaging ($^1$H-MRI) on days 3 (acute) and 56 (chronic) following I/R injury, unless noted otherwise. Four dogs died within the first 2 hours of establishing reperfusion (despite resuscitation efforts) and in two dogs, reperfusion was not established due to the failure of occluder implementation. The remaining dogs were assigned to two different groups—Controls (n=3) and Infarcted (n=14). The control group underwent the surgical procedure (shams), but was not subjected to I/R injury. The infarcted group underwent 3 hours of no-flow ischemia followed by reperfusion. Among the infarcted dogs, three dogs were sacrificed on day 3 for histological validation of acute hemorrhagic infarctions. All the results (except histological evidence for acute hemorrhagic infarctions) were obtained from the remaining 11 dogs of the infarcted group and 3 dogs of the control group that were sacrificed immediately following the chronic phase MRI study.

In-Vivo $^1$H-MRI Studies

All $^1$H-MRI studies on animals were performed on a clinical 1.5 T MRI system (MAGNETOM Espree, Siemens Medical Solutions, Erlangen, Germany) equipped with a high-performance gradient system (maximum gradient amplitude of 40 mT/m, maximum slew rate of 200 T/m/s). The animals were anesthetized, intubated and ventilated as described before for the surgical procedure. They were placed on the scanner table in feet-first, right anterior position. A flexible eight-channel phased-array surface coil was placed on their chests for signal reception. $B_1$ field changes were transmitted using the scanner's integrated body coil. Scout images were acquired to localize the heart and a volume-selective shim covering the whole heart was performed to minimize off-resonance artifacts. Multiple cardiac-gated breath-held 2D images of contiguous short-axis sections covering the entire left-ventricle (LV) and the three long-axis views (2 chamber, 3 chamber and 4 chamber) were acquired using cardiac phase resolved SSFP (cine-SSFP), T2*-weighted imaging and Late Enhancement (LE) imaging. Multi-gradient echo (T2*-weighted) and LE images were acquired at mid-diastole when the cardiac motion is minimal. Cardiac gating was achieved by using prospective ECG triggering and breath-holding was achieved by suspending ventilation at end-expiration. Anesthesia was carefully controlled during breath-holding to avoid any spontaneous breathing. A 2-3 minute rest period between successive breath-holds was given to maintain the heart rate at a constant level throughout all acquisitions.

Cardiac wall motion was visually assessed using cine-SSFP images. Typically used cine imaging parameters were TR/TE=3.5/1.75 ms, flip angle=70°, 20-25 cardiac phases per imaging section and readout bandwidth (BW)=930 Hz/pixel. Significant wall motion abnormalities were observed in the LAD territories of infarcted dogs both during acute and chronic phase MRI studies. Acute hemorrhage and chronic iron loading were evaluated using T2*-weighted images acquired by a multiple gradient-echo sequence. Typically used imaging parameters were TR=220 ms, 12 echoes with TEs=3.4, 6.4, 9.4, 12.4, 15.4, 18.4, 21.4, 24.3, 27.3, 30.3, 33.3 and 36.3 ms, flip angle=12° and BW=566 Hz/pixel. All in-vivo imaging studies were terminated with the acquisition of Phase-Sensitive Inversion Recovery LE images using a non-selective inversion recovery (IR) prepared SSFP sequence. Initially, 0.2 mmol/kg of Gadolinium-DTPA contrast agent (Magnevist, Bayer Healthcare Pharmaceuticals Inc., Wayne, N.J.) was administered intravenously using a power injector followed by a 10 ml saline flush. An optimal inversion time (TI) to null the apparent normal myocardium was then determined from TI scout images. LE images were acquired 10-15 minutes after contrast administration using the following imaging parameters: TR/TE=3.5/1.75 ms, flip angle=40° and BW=1002 Hz/pixel. Other commonly used imaging parameters for all the scans were Field-of-view (FOV)=166 mm×280 mm, imaging matrix=116×192, imaging section thickness=8 mm and number of averages=1. FOV was rectangular for all the scans. No image acceleration methods were used.

All animals in the infarcted group sustained acute hemorrhagic infarctions as indicated by the acute phase T2*-weighted and LE images. All animals in the control group did not sustain any myocardial infarction throughout the study as verified by both acute and chronic phase LE images.

Ex-Vivo $^1$H-MRI Studies

Animals were euthanized immediately after the chronic phase MRI study by intravenously administering 0.2 ml/kg body weight of Euthasol (390 mg/ml sodium pentobarbital and 50 mg/ml phenyloin sodium) and their hearts were excised. Each heart was manually sliced into 1 cm thick slices along the LV short-axis. Each slice was immersed in 0.05M Phosphate-buffered saline (PBS; pH=7.4) and ex-vivo 2D T2*-weighted and Phase-Sensitive Inversion Recovery LE images were acquired using a multiple gradient-echo sequence and IR-prepared SSFP sequence respectively. A head coil was used for signal reception for ex-vivo imaging. Typical imaging parameters used for ex-vivo T2*-weighted and LE images were the same as those used for the corresponding in-vivo T2*-weighted and LE images. The imaging section was carefully selected to avoid any partial-voluming between the myocardial tissue and the PBS bath. FOV was rectangular and no image acceleration method was used.

Patient $^1$H-MRI Studies $^1$H-MRI studies were performed on patients (n=15, 3 females) according to the protocols approved by the Institutional Review Board. Patients with acute ST-elevated myocardial infarction meeting American Heart Association diagnostic criteria were enrolled in the study only if successful percutaneous coronary intervention (PCI) was performed within 12 hours of the onset of symptoms. Patients were excluded from the study if they had previous myocardial infarctions or were contraindicated for a cardiac MRI study. All enrolled patients underwent $^1$H-MRI 3 days after successful PCI and again at 6 months after initial enrollment.

All patient imaging studies were performed on a clinical 1.5 T MRI system (MAGNETOM Avanto, Siemens Medical Solutions, Erlangen, Germany) equipped with high-performance gradient system (maximum gradient amplitude of 45 mT/m and maximum slew rate of 200 T/m/s). $B_1$ field was transmitted using the scanner's integrated body coil and an eight-channel flexible phased-array coil was placed on the chest for signal reception. All anatomical axes were localized and a volume-selective shim covering the whole heart was performed. Contiguous short-axis sections covering the entire LV along with 2, 3 and 4 chamber long-axis views of the heart were acquired at mid-diastole using cine-SSFP, Multi-gradient echo (T2*-weighted) and LE imaging. Typical imaging parameters used for cine-SSFP images were TR/TE=3.32/1.16 ms, flip angle=65°, BW=930 Hz/pixel, 25 cardiac phases, FOV=340 mm×276 mm, imaging matrix=192×156, imaging section thickness=10 mm and number of averages=1. T2*-weighted images were acquired using a multiple gradient-echo technique. Typical imaging parameters used for T2*-weighted images were TR=240 ms, 8 echoes with TEs=2.6, 4.8, 7.0, 9.3, 11.5, 13.7, 16.0 and 18.2 ms, flip angle=10°, BW=355 Hz/pixel, FOV=420 mm×328 mm, imaging matrix=256×200, imaging section thickness=10 mm and number of averages=1. LE images were acquired 10-15 minutes after an intravenous Gadolinium-DTPA administration (0.2 mmol/kg of body weight) using an optimal TI to suppress signal from remote myocardium. An IR-prepared fast low angle shot (FLASH) sequence was employed with the typical imaging parameters being TR=1 R-R interval, TE=3.32 ms, BW=235 Hz/pixel, FOV=400 mm×300 mm, imaging matrix=256×192, imaging section thickness=10 mm and number of averages=1. FOVs were rectangular and no image acceleration method was used.

Gross Histological Identification of Myocardial Infarcts

All ex-vivo myocardial slices from every animal were stained with triphenyltetrazolium chloride (TTC) to histochemically validate irreversible myocardial damage and delineate the infarcted territories from the viable myocardium. TTC stains viable myocardium brick-red as membrane-bound dehydrogenases and other cofactors reduce the tetrazolium salts to a brick-red formazan pigment, while infarcted myocardium remains unstained. Briefly, the slices were incubated in 1% (w/v) TTC in PBS at 37° C. for 15-20 minutes and photographed under room light. Chronic iron overloading appears yellowish-brown within the pale infarcted territories. All infarcted dogs contained a number of slices with TTC-unstained infarct regions within the LAD territory of LV. Few slices were negative for infarction and were discarded. All slices from the control dogs were negative for infarction.

Semi-Automatic In-Vivo Image Analysis

Figure 11:
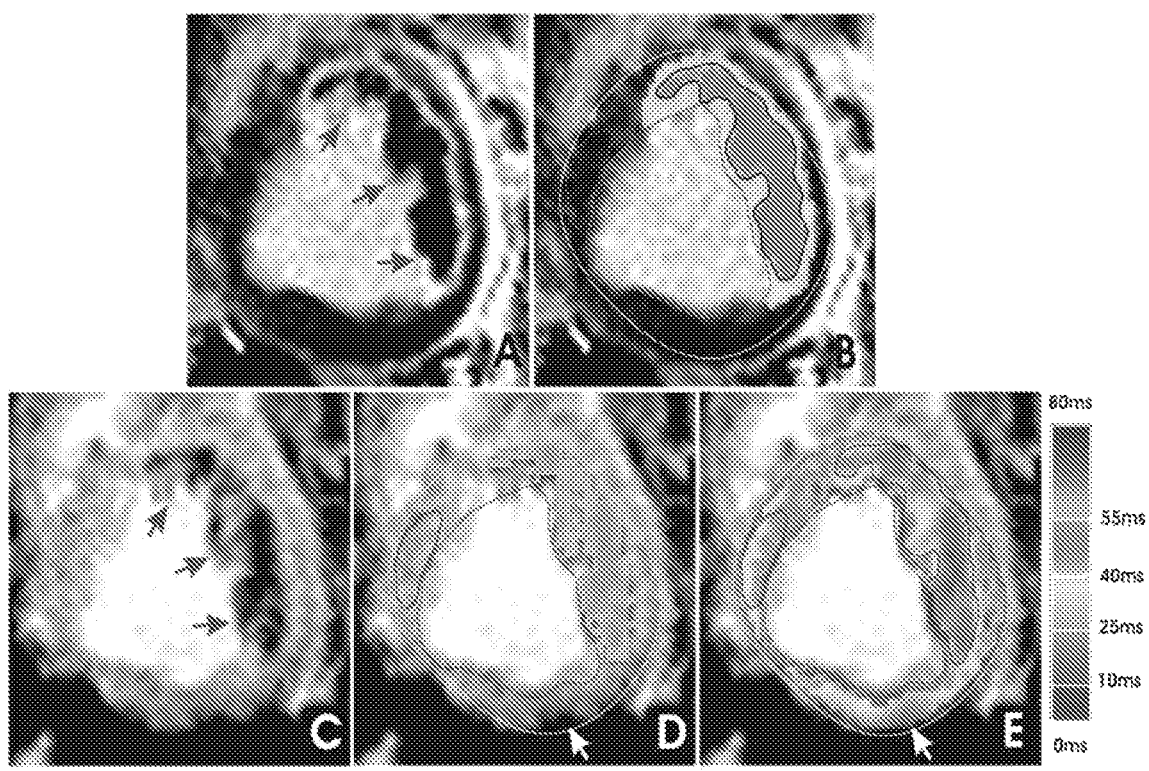
FIG. 11 depicts the semi-automatic threshold-based analysis of images acquired from an infarcted dog during acute phase (day 3) MRI studies. (A) Representative Late enhancement (LE) image showing gadolinium hyperenhanced infarcted region (red arrows) with microvascular obstruction (MVO; dark region) enclosed within. (B) Infarcted myocardium (highlighted yellow pixels on the LE image from (A)) identified as the hyperintense region with mean signal intensity (SI) 5 standard deviations (SDs) greater than that of reference ROI (blue ROI). MVO (orange region) was included in the final analysis of infarcted myocardium. (C) Representative T2*-weighted image acquired at TE=18.38 ms showing hypointense hemorrhagic myocardium (red arrows). (D) Hemorrhagic myocardium (highlighted blue pixels on the T2*-weighted image from (C)) identified as the region with mean SI 2 SDs lesser than that of reference ROI (blue ROI). Region affected by off-resonance artifacts (white arrow) was not included in the analysis. (E) Color-coded T2* map showing the hemorrhagic myocardium (bright red region within a red ROI). Region affected by off-resonance artifact (white arrow) was excluded.

All in-vivo image analyses (both acute and chronic from animals and patients) were performed off-line using validated and certified cardiac MR image processing software (cmr$^{42}$, Circle Cardiovascular Imaging Inc., Calgary, AB, Canada). To minimize unwanted off-resonance and flow artifacts, in-vivo T2* maps were constructed by fitting the multi-echo data from only the first 6 echoes (TEs from 3.4-18.4 ms for animals and 2.6-13.7 ms for patients) to a mono-exponential decay. Endocardial and epicardial contours were drawn for each imaging section on the cine-SSFP image corresponding to the appropriate mid-diastolic phase. The contours were then copied on to both T2*-weighted and LE images and adjusted when necessary. Remote myocardium was identified as the region showing no hyperintensity on LE images. A reference region-of-interest (ROI) was drawn in the remote myocardium and a threshold based semi-automatic method was used to detect infarcted myocardium on LE images. Infarcted myocardium was defined as the hyperintense region on LE images with ≥10 adjacent pixels having mean signal intensity (SI) 5 standard deviations (SD) greater than the mean SI of reference ROI (45). In the final analysis of infarcted myocardium on LE images, regions of hypointense territories (microvascular obstruction) within the hyperintense territories were manually included. Refer to FIG. 11

Figure 13:
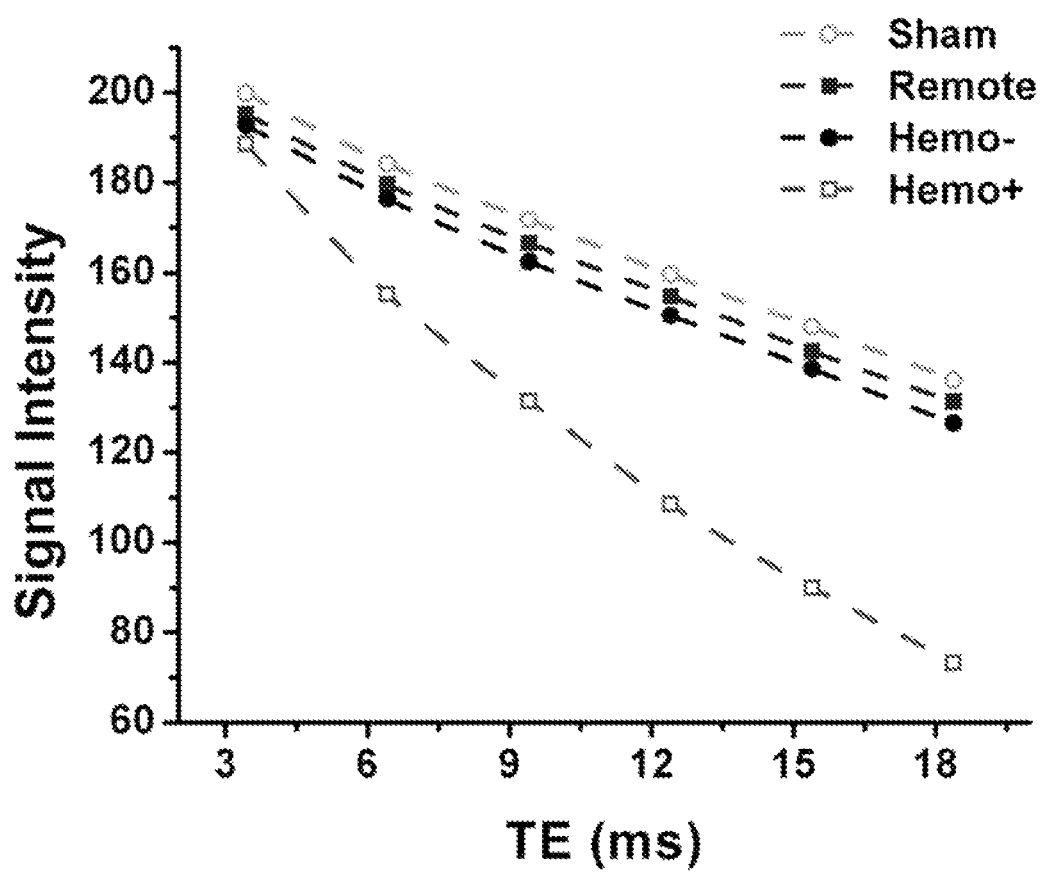
FIG. 13 depicts the monoexponential fits of multi-echo data from T2*-weighted images. Representative monoexponential fits for Sham (T2*=2.1 ms), Remote (T2*=40.7 ms), Hemo+(T2*=19.1 ms) and Hemo− (T2*=39.6 ms) myocardium are shown.

The reference ROI from the LE image was copied on to the T2*-weighted image acquired at the longest TE among all the echoes used to construct the T2* map (FIG. 13), i.e. TE=18.4 ms for animals and TE=13.7 ms for patients. Hemorrhagic myocardium was identified on this image as the hypointense region with ≥10 adjacent pixels having mean SI at least 2 SDs below the mean SI of the reference ROI (46). While drawing the reference ROI and in the final analysis of the hemorrhagic myocardium, care was taken not to include regions affected by blooming artifacts arising from susceptibility shifts at the heart-lung interface. Also, any hypo-intense region lying outside the infarcted territory was excluded from the analysis.

Classification of In-Vivo Imaging Sections

For animals, all in-vivo imaging sections were divided into three different groups based on in-vivo LE and T2*-weighted images. Myocardial imaging sections that contained hyper-intense LAD infarct regions on LE images with a hemorrhagic core on the corresponding T2*-weighted images were classified as hemorrhagic infarct sections. Similarly, imaging sections that contained LAD infarct regions on LE images but no hemorrhagic core on the corresponding T2*-weighted images were classified as non-hemorrhagic infarct sections. Imaging sections that did not contain any infarcted regions were not used for further analysis. Imaging sections from the control dogs (no patients) were classified as Sham. Mean per-section in-vivo T2* values were measured for hemorrhagic infarct (Hemo+), non-hemorrhagic infarct (Hemo−), remote myocardium (Remote) and sham myocardium (Sham) from the corresponding T2* maps (in-vivo T2*$_{section}$). Also, mean whole-heart in-vivo T2* values were measured for each heart from Hemo+, Hemo−, Remote and Sham groups by averaging across the corresponding imaging sections (in-vivo T2*$_{heart}$).

For patients, a similar classification of in-vivo imaging sections was used and in-vivo T2* values on a per-section and whole-heart basis were measured for Hemo+, Hemo− and remote groups (no shams) from the corresponding T2* maps.

Semi-Automatic Ex-Vivo Image Analysis and Classification

All ex-vivo image analysis was also performed offline using cmr$^{42}$. T2* maps for each ex-vivo myocardial slice from all the animals were constructed by fitting multi-echo data from only the first 6 echoes (TEs 3.4-18.4 ms) to a mono-exponential decay. Remote myocardium was defined as the region stained brick-red by TTC along with the absence of hyperintensity on ex-vivo LE image. A reference ROI was drawn within the remote myocardium on LE image and infarcted myocardium was defined as the region with ≥10 adjacent pixels having mean SI at least 5 SDs above the mean SI of the reference ROI. Subsequently, the reference ROI was copied on to the T2*-weighted image acquired at TE=18.4 ms. Hemorrhagic myocardium was defined as the region with ≥10 adjacent pixels having a mean SI at least 2 SDs below the mean SI of the reference ROI.

On the basis of ex-vivo LE and T2*-weighted images, as well as corresponding TTC staining, all ex-vivo myocardial slices were also classified as sham, hemorrhagic infarct or non-hemorrhagic infarct slices as earlier (refer to in-vivo image analysis). Excellent correlation between TTC-unstained infarcted region and hyperintense infarcted region on LE images was observed. Slices from the infarcted dogs that did not contain TTC-unstained infarcted regions or hyperintense regions on corresponding ex-vivo LE images were discarded. Mean per-slice ex-vivo T2* values for hemorrhagic infarcts (Hemo+), non-hemorrhagic infarcts (Hemo−), remote myocardium (Remote) and sham slices (Sham) were measured from T2* maps (ex-vivo T2*$_{slice}$). Also, mean whole-heart ex-vivo T2* values for each dog were measured for Hemo+, Hemo−, Remote and Sham groups by averaging across all the corresponding slices (ex-vivoT2*$_{heart}$).

Isolation of Tissue Samples

From both ex-vivo hemorrhagic and non-hemorrhagic infarct slices, unstained TTC sections (only from the densely infarcted areas) were carefully cut out. Care was taken not to cut into the infarct border zone or any surrounding TTC-stained viable myocardium. To accommodate further tissue analysis, all blocks of hemorrhagic and non-hemorrhagic infarcts were further cut into their constituent smaller hemorrhagic (Hemo+) and non-hemorrhagic (Hemo−) infarct samples (0.5-0.8 cm$^3$). Similarly, from each hemorrhagic and non-hemorrhagic infarct slice, at least 2 samples of TTC-stained viable myocardium were cut out (Remote). From each sham slice (obtained from control dogs), at least two samples of TTC-stained normal myocardium were cut out (Sham). An average of 30 myocardial samples was obtained from each infarcted dog; while an average of 10 samples was obtained from each control dog. In all nearly 360 samples were obtained and analyzed for the entire study.

Histopathological Studies

A representative myocardial sample from each of the Hemo+, Hemo−, Remote and Sham groups was obtained from every infarcted and control dog. The sample was dehydrated, embedded in a paraffin block and three contiguous 5 μm sections were obtained using a microtome. The three sections were stained with regressive Hematoxylin and Eosin (H & E), Masson's Trichrome and Perl's stains respectively using standard techniques. The sections were mounted on glass slides and scanned at 100× magnification using an ACIS II technology based ChromaVision digital slide scanner (Clarient Inc., Aliso Viejo, Calif.). The slides were also imaged at 400× magnification using an Olympus BX41 stereo compound microscope with dual view side (Olympus America Inc., Center Valley, Pa.).

H & E staining was used to distinguish between necrotic and viable myocardium. Hematoxylin stained nuclei of viable cells blue, while eosin stained the cytoplasmic structures pinkish red. Acute infarcted myocardium showed massive infiltration of inflammatory cells. Extravasated red blood cells (eosinophilic structures) in hemorrhagic infarctions were stained intensely red by eosin. Chronic infarcted myocardium was stained faint pink with no distinctly visible individual cells.

Masson's trichrome staining was used to identify collagen deposition within the infarcted myocardium. Viable myocardium was stained dark red, while collagenous scar was stained intensely blue. Perl's staining was used to visually identify iron deposition within the infarcted myocardium. Iron deposits externalized from the extravasated red blood cells were stained blue, while cells and cytoplasmic structures were stained pink.

Capacitor Cell Design and Electrical Impedance Measurements

Bulk electrical impedance of each tissue sample from Hemo+, Hemo−, Remote and Sham groups were measured using two-terminal electrode technique as previously described by Schwan (*Physical techniques in biological research. Volume VI, Electrophysiological methods*. Part B, W. L. Nastuk, Ed. (Academic Press, New York; London, 1963), pp. 323-407.). A capacitor cell, with a variable electrode distance similar to that described by Schwartzman et al (*J Interv Card Electrophysiol* 3, 213 October, 1999), was designed to measure bulk electrical impedance of each sample using alternating-current (AC) impedance spectroscopy. The capacitor cell consisted of a transparent tubular glycol-modified polyethylene teraphthalate (PETG) body that is closed at one end and fitted with a removable Delrin cap at the other end. Two square silver electrodes, each of 1.5 cm² surface area, were enclosed in the tubular body. One electrode was affixed to the closed end, while the other electrode was affixed to a PETG disk that can move through the tubular body. The electrodes were soldered to the inner conductors of copper coaxial cables, which in turn were connected to the analyzer. The outer conductors were connected to electrical ground.

Each sample was incubated at 37° C. for 15 minutes prior to use. The sample was then sandwiched between the two electrodes of the capacitor cell and 10 μA of alternating current was passed parallel to the myocardial fibers. The voltage that developed across the sample was measured using Solartron 1260 impedance/gain-phase analyzer (Solartron Instruments, Hampshire, UK) and acquired using ZPlot data acquisition software. The induced voltage was divided by the current passed to derive the complex AC-impedance (Z in ohms) of the sample. The impedance values were measured at frequencies ranging from 100 Hz to 10 MHz with 10 measurements in each frequency decade. Stray effects in the measurements were corrected using methods described by Schwan (above). To minimize the effects of α-dispersion (Schwan and Kay, *Ann NY Acad Sci* 65, 1007 Aug. 9, 1957) (occurring around 100 MHz) and undesired myocardial sample preparation errors (such as an inhomogeneous sample containing both infarct region and surrounding viable myocardium), all analysis was limited to impedance data acquired at 1 MHz.

Normalized Conductivity and Permittivity Measurements

Bulk electrical permittivity and conductivity of each sample were derived from the AC-impedance measurements. Surface area (A in m²) and distance between the electrodes (d in m) after the sample is placed between the electrodes were measured. The complex admittance Y (in Siemens S) of the sample was calculated as the reciprocal of Z, which can be further expressed as follows (S. Grimnes, M. Ø. G., in *Bioelectricity and Bioimpedance Basics*. (Academic Press, London, U. K., 2008), pp. 57-92)

$$Y = G + i\omega C$$

where G is the conductance (in S), C is the capacitance (in F), $\omega$ is the angular frequency (in rad/s) and i is $\sqrt{-1}$ G and C can be further expressed as follows $$G = \frac{A \times \sigma}{d}$$

$$C = \frac{A \times \varepsilon}{d}$$

where $\sigma$ and $\varepsilon$ are bulk conductivity (in S/m) and permittivity (in F/m) respectively. Bulk $\sigma$ and $\varepsilon$ of each sample were therefore calculated from the original complex impedance data (Z) as follows $$\sigma = \frac{\mathrm{Re}\left(\frac{1}{Z}\right) \times d}{A}$$

$$\varepsilon = \frac{\mathrm{Im}\left(\frac{1}{Z}\right) \times d}{A \times \omega}$$

For a given heart from an infarcted dog, mean conductivity ($\sigma'_{Remote}$) and permittivity ($\varepsilon'_{Remote}$) of its remote myocardium were calculated by weight-averaging the conductivities and permittivities of all its constituent remote samples as follows $$\sigma'_{Remote} = \frac{\Sigma(\sigma_{Remote} \times W_{Remote})}{\Sigma W_{Remote}}$$

$$\varepsilon'_{Remote} = \frac{\sum(\varepsilon_{Remote} \times W_{Remote})}{\sum W_{Remote}}$$

where $\sigma_{Remote}$ and $\varepsilon_{Remote}$ are the individual conductivity and permittivity of each constituent remote sample of a heart and $W_{Remote}$ is its corresponding sample weight. Normalized conductivity ($\bar{\sigma}_{sample}$) and permittivity ($\bar{\varepsilon}_{sample}$) of each Hemo+, Hemo− and Remote sample from the heart were then derived as follows:

$$\bar{\sigma}_{sample} = \frac{\sigma_{sample}}{\sigma'_{Remote}}$$

$$\overline{\varepsilon}_{sample} = \frac{\varepsilon_{sample}}{\varepsilon_{Remote}}$$

Also, per-slice normalized conductivity ($\overline{\sigma}_{slice}$) and permittivity ($\overline{\varepsilon}_{slice}$) were calculated for the Hemo+, Hemo−, Remote and Sham groups by weight-averaging $\overline{\sigma}_{sample}$ and $\overline{\varepsilon}_{sample}$ respectively from their constituent samples.

Local Iron Deposition Measurements

The extent of iron (Fe) deposition within each myocardial sample from the Hemo+, Hemo−, Remote and Sham groups was analyzed using Inductively Coupled Plasma-Mass Spectrometry (ICP-MS) (J. P. Carpenter et al., *Circulation* 123, 1519 Apr. 12, 2011). The samples were briefly rinsed with ultrapure double-distilled deionized (Milli-Q) water (resistivity of 18 MΩ-cm at 25° C.), blotted, weighed and placed in individual autoclavable Teflon centrifuge tubes (Thermo-Fisher Scientific, Waltham, Mass.). The Teflon tubes were soaked in 3% nitric acid overnight and rinsed with Milli-Q water before use. 2 ml of 69% (w/v) tracemetal grade nitric acid (GFS Chemicals Inc., Columbus, Ohio) was added to the samples and vented. The samples were then microwave digested using a Milestone EthosEZ closed microwave digestion system (Milestone S.r.l., Bergamo, Italy) equipped with temperature and pressure sensors (maximum temperature of 260° C. and maximum pressure of 10 MPa). The digestion temperature was ramped up at 12° C./min and maintained at 120° C. for 10 minutes before allowing to cool down to room temperature. The digested samples were then filtered through 0.45 μm Teflon syringe-filters (Thermo-Fisher Scientific) and the filtrates were collected in individual 15 ml metal-free polypropylene tubes (VWR International Inc., Bridgeport, N.J.). The filtrates were diluted to 1:40 of original concentration with Milli-Q water and an internal standard mixture (CPI International, Santa Rosa, Calif.) containing Sc, Tb, Y, In and Bi was added. A set of standards with concentrations ranging from 0 ppb to 100 ppb was prepared using a mixed element solution (CPI International, Santa Rosa, Calif.). All samples and standards were prepared in duplicates in a 2% nitric acid matrix.

All samples were analyzed on a quadrupole based X Series 2 ICP-MS (Thermo-Fisher Scientific) equipped with Collision Cell Technology to reduce interference from doublets. Samples were introduced into the ICP-MS at a rate of 0.5 ml/min using an automated SC-FAST system (Elemental Scientific Inc, Omaha, Nebr.) comprising of an autosampler, diaphragm vacuum pump, PFA-ST nebulizer and a Peltier-cooled cyclonic spray chamber. Data was acquired using the dedicated PlasmaLab software. Fe content measured within each sample was averaged between the two duplicates and expressed as 1 μg of Fe per g of sample ($Fe_{sample}$). Also, per-slice Fe content of Hemo+, Hemo−, Remote and Sham groups ($Fe_{slice}$) were measured by weight-averaging $Fe_{sample}$ of their constituent samples.

Statistical Analysis

All statistical analyses (both animals and patients) were performed using STATA 10.1 (StataCorp, College Station, Tex.). All data are expressed as Mean±SD. For animals, ex-vivo $T2^*_{slice}$ (per-slice ex-vivo T2*), $Fe_{sample}$ (Fe content within myocardial sample), $\overline{\sigma}_{sample}$ and $\overline{\varepsilon}_{sample}$ were compared among Hemo+, Hemo−, Remote and Sham groups using mixed-model linear regression. The null hypothesis was that there was no difference in each tested parameter among the four different groups. Since differences among the animals were of no interest, canines were entered as random effects. Samples from each heart (or myocardial slice) were nested in the analysis to account for repeated measurements from a single heart (or myocardial slice). The relationship between in-vivo $T2^*_{heart}$ (from both acute and chronic phase MRI studies) and the corresponding ex-vivo $T2^*_{heart}$ was analyzed using mixed-model linear regression. Similarly, the relationships of log(ex-vivo $T2^*_{slice}$) with . . . log($Fe_{slice}$), $\overline{\sigma}_{sample}$ and $\overline{\varepsilon}_{sample}$ with log($Fe_{sample}$), $\overline{\sigma}_{slice}$ and $\overline{\varepsilon}_{slice}$ log(ex-vivo $T2^*_{slice}$) were analyzed. The null hypothesis was that there was no linear relationship between the tested parameters.

Similarly, for patients, mixed-model linear regression was used to compare in-vivo $T2^*_{section}$ among the Hemo+, Hemo− and Remote groups. The null hypothesis was that there was no difference in in-vivo $T2^*_{section}$ among the three different groups. Patients were entered as random effects and repeated measurements from each heart (or imaging section) were accounted for by nesting the measurements for analyses. The relationship between mean in-vivo $T2^*_{heart}$ from acute and chronic phase MRI studies was analyzed using mixed-model linear regression. The null hypothesis was that there was no linear relationship between mean in-vivo $T2^*_{heart}$ from acute and chronic phase MRI studies. A two-tailed p-value<0.05 was considered to be statistically significant for all animal and patient data analyses.

Example 2

Free-Breathing, ECG-Triggered, Dark-Blood Prepared 3D T2* MRI

Breath-held, ECG-triggered, 2D T2* mapping at 1.5 T is the current standard for identifying iron overload in the heart. However, this approach has a number of limitations for our application: (i) Our early studies and the literature suggest that, in the setting of large infarcts, breath holding may trigger arrhythmias. In our experience, repetitive breath-held image acquisitions have led to fatal arrhythmias in canines with hemorrhage; and non-fatal arrhythmias demand undesirably long breath holding times; (ii) Partial volume effects in the through-plane direction can significantly reduce the conspicuity of the regions with an iron overload; (iii) Bright blood T2* maps are prone to significant image artifacts (ghosts and smears), particularly when TEs are long. At 1.5 T, the sensitivity for visualizing smaller iron depositions can be limited and require the use of longer TEs in spite first-order flow compensation at every TE. Doubling the field strength is known to increase the image contrast for detecting iron particulates by a factor of 4, which in turn implies that significantly shorter TEs may be used to generate T2* maps. Flow compensation at shorter TEs and dark-blood imaging may be ideal for overcoming these artifacts. The current approach also has limited signal-to-noise (S/N) characteristics. 3D mGRE acquisitions, particularly when performed at 3.0 T, can increase the S/N and permit the use of image acceleration strategies to reduce scan time without compromising S/N.

To overcome these limitations we propose a navigator-gated, double inversion recovery prepared 3D multi gradient echo (mGRE) sequence so that significantly artifact-reduced, free breathing, high-resolution, T2* maps can be generated. The timing diagram for this imaging sequence is shown in FIG. 1.

Example 3

Detecting Acute Myocardial Reperfusion Hemorrhage (aMRH) with MRI

T2 and T2* MRI have both been shown to be sensitive for detecting aMRH. However, there is (i) no consensus on which of the two methods yield the most desirable means for detecting aMRH, and (ii) no histology studies that confirm T2 or T2* MRI can and do identify myocardial hemorrhage (O'Regan D P, Ahmed R, Karunanithy N, et al. Reperfusion hemorrhage following acute myocardial infarction: assessment with T2* mapping and effect on measuring the area at risk. Radiology 2009; 250:916-922. Ganame J, Messalli G, Dymarkowski S, et al. Impact of myocardial haemorrhage on left ventricular function and remodelling in patients with reperfused acute myocardial infarction. Eur Heart J 2009; 30:1440-1449). The inventors determined the optimal quantitative MRI approach for detecting a MRH and to validate that iron composites are found within hemorrhagic infarctions on the basis tissue histology.

Ischemia reperfusion injury (3 hour occlusion of LAD followed by reperfusion) was inflicted in canines (n=9). Serial MRI studies (T2 and T2* mapping, and delayed enhancement (DE)) were performed post-reperfusion on days 2, 5 and 7. Hemorrhagic infarctions (MH+) were determined by the presence of hypointense territories on T2* maps within the infarcted zones identified from DE images. In the MH+ group, ROIs from the T2* maps around the hemorrhagic cores and remote territories were copied onto the T2 maps. In non-hemorrhagic infarctions (MH−), manually drawn ROIs on DE images around the infarcted zones and remote territories were copied onto T2 and T2* maps. T2 and T2* values from the MH+, MH− and remote territories were measured and compared (p<0.05). Animals were sacrificed on day 7 and TTC staining and histological analysis (H&E and Prussian blue) was performed.

Figure 2:
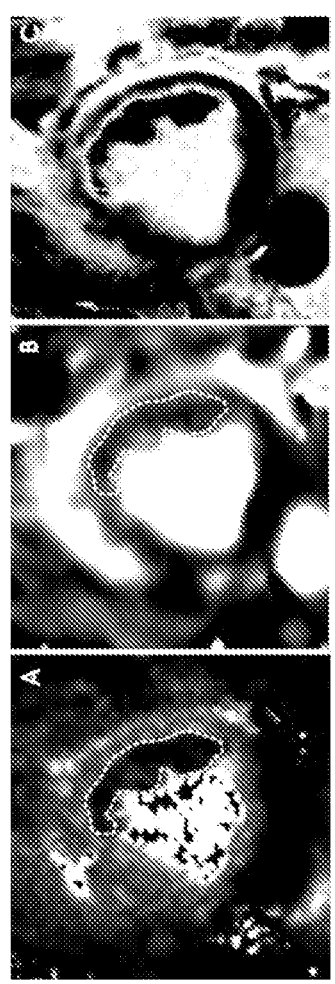
FIG. 2 depicts cardiac MRI images showing sensitivity for detection of hemorrhage. This figure depicts an example of short-axis T2* map (A), T2 map (B) and DE image (C) from a dog on day 2 post-reperfusion. Manually traced ROI (yellow boundary) around the hemorrhagic territory are shown. T2* changes, compared to T2 changes, were more pronounced in the presence of hemorrhage. DE MRI showed the area of MI and the extent of microvascular injury (hyperintense core). Similar results were observed on days 5 and 7.
Figure 3:
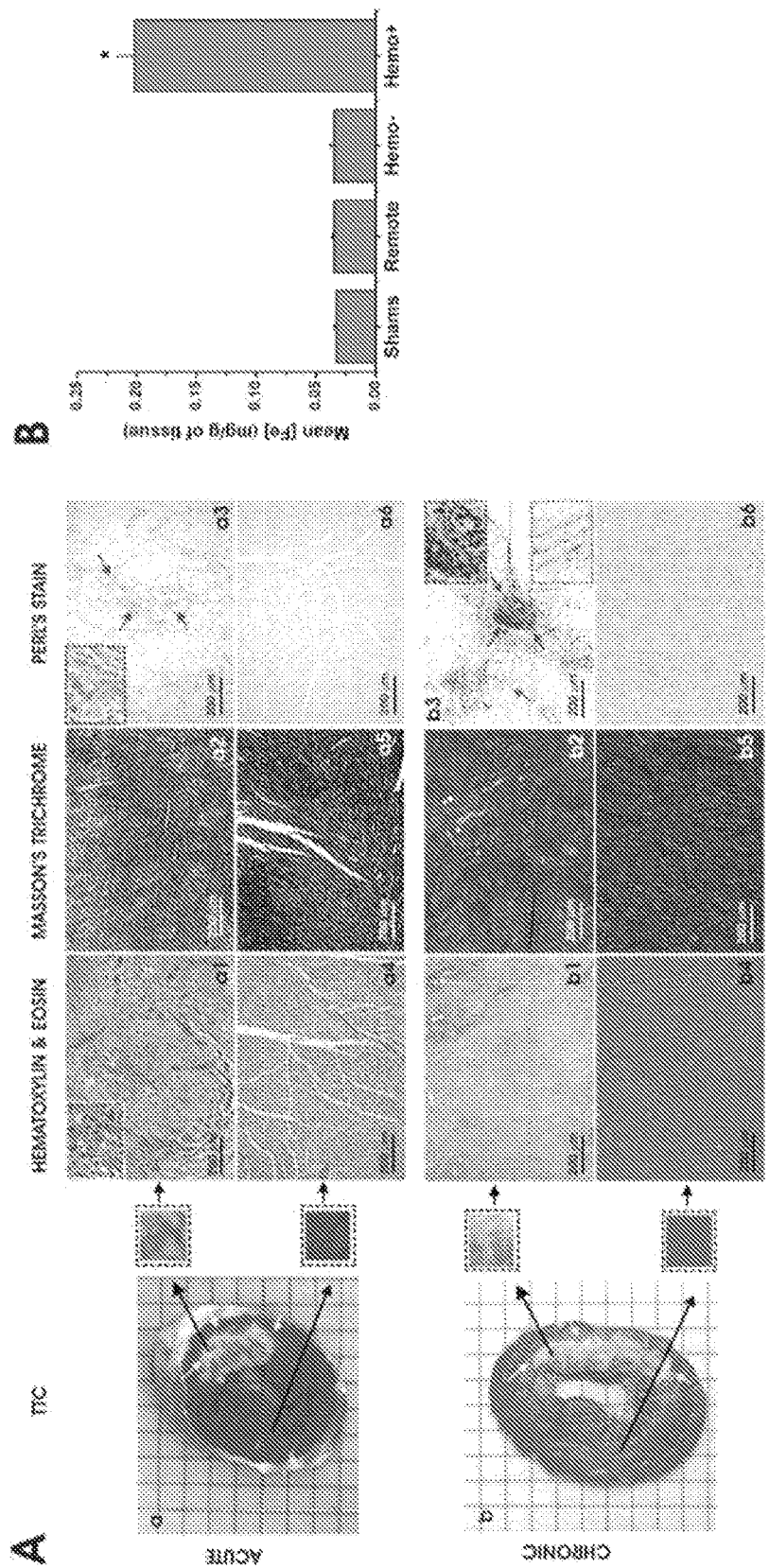
FIG. 3 depicts chronic iron deposition in hemorrhagic myocardial infarction. (A) Gross histochemical staining (TTC) of short-axis sections of hearts show the site of myocardial infarction (pale color, yellow arrows) in acute and chronic reperfusion injury. The acute section shows blood within the necrotic tissue and the chronic section shows yellow-brown stain within the necrotic tissue. Microstructural histopathology (100× magnification) of acute infarct (a1-a6) and corresponding remote sections show extravasation of red blood cells (Hematoxylin & Eosin, yellow arrows, inset), early deposition of collagen (Masson's Trichrome) and iron (Perl's stain, black arrows, inset) in the infarcted section (not observed in remote territories). Histopathology (100× magnification) of chronic infarct (b1-b6) and corresponding remote sections show grossly damaged myocardium (Hematoxylin & Eosin), dense deposition of collagen (Masson's trichrome) and iron (Perl's stain, black arrows, inset) in the infarcted section (not observed in remote territories). Insets show detailed views of tissue structures collected from regions indicated by arrows. Note the presence of iron among cardiomyocytes in incompletely infarcted sites (lower inset of b3) (B) ICP-MS analysis of myocardial tissue obtained from Shams, Remote, Hemo-, and Hemo+ sections on day 56 post reperfusion (chronic) showed significantly higher amount of iron in Hemo+ compared to all other sections (*, p<0.001).

MH was observed in 7 dogs, but not in the remaining 2 dogs. FIG. 2 shows a representative set of T2* and T2 maps and the corresponding DE image in an animal with aMRH. Table 1 lists the respective values and the change in T2 and T2* between MH+, MH−, and remote territories. TTC stains and histology results are shown in FIG. 3A (a, a1-a6). TTC confirmed the infarction; and histology confirmed the presence of pooled red blood cells and iron within regions of reperfused infarcts.

TABLE 1

Mean T2* and T2 values of hemorrhagic (MH+), non-hemorrhagic (MH−) and remote territories averaged across all animals and study days are shown. Percentage T2* and T2 changes of MH+ and MH− are computed relative to remote myocardium. T2* of MH+ decreased significantly compared to MH− and remote myocardium. T2 of both MH+ and MH− was significantly higher relative to remote myocardium. Only T2* changes were statistically lower than remote regions (t-test, $p < 0.05$).

| | Region | | | | |
|---|---|---|---|---|---|
| | | | | % Change | |
| Technique | Remote | MH+ | MH− | MH+ | MH− |
| T2* (ms) | 41 ± 5 | 23 ± 5 | 43 ± 6 | −42 ± 14% | 8 ± 17% |
| T2 (ms) | 55 ± 6 | 62 ± 5 | 72 ± 4 | 13 ± 14% | 35 ± 11% |

T2* of MH+ territories were significantly lower than the T2* of MH− and remote territories. This was not the case in T2 maps. The reduced conspicuity of MH on T2 maps is likely due to its intrinsic sensitivity to myocardial edema. The insensitivity of T2* MRI to edema and strong sensitivity to hemorrhage makes T2* maps the most effective method for detecting a RMH. Histological evidence confirmed that the hypointense regions within infarcted myocardium in T2* MRI are hemorrhagic. These results support our hypothesis that T2* MRI is suited for noninvasive identification of myocardial hemorrhage in vivo.

Example 4

Iron Deposition Electrical Properties of Myocardial Infarcts

Previous studies have shown that introducing highly conductive particulates into an otherwise poor dielectric medium acts to enhance the bulk electrical permittivity of the medium. Since magnetite crystals have a relatively high electrical conductivity (approximately $2.5 \times 10^4$ S/m at the physiologic temperature), pathological elevations of it within localized regions of the heart muscle (with conductivity <1 S/m may act to increase the electrical permittivity of infarcted myocardial tissue.

Figure 6:
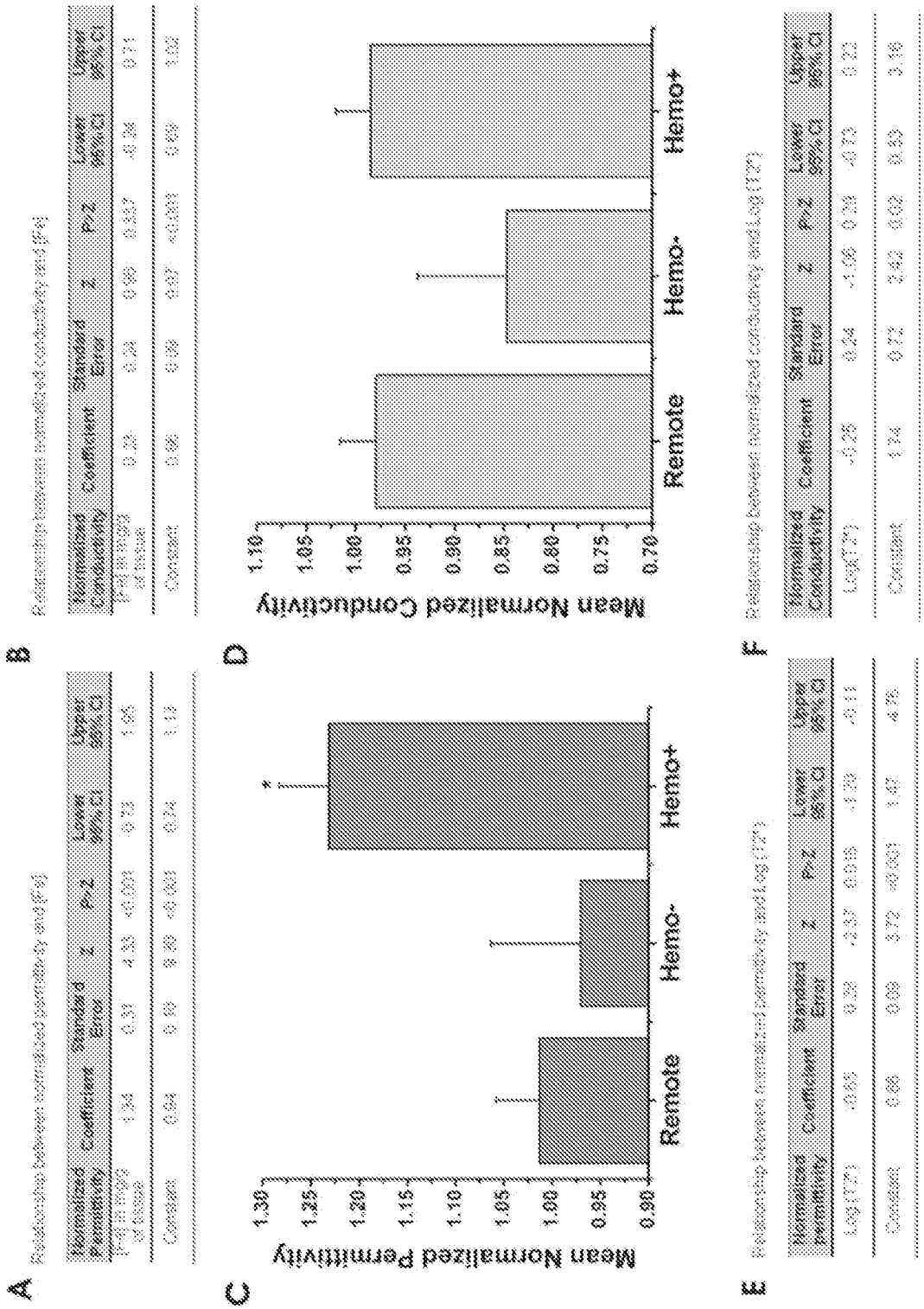
FIG. 6 depicts iron deposition increases electrical capacitance of chronic myocardial infarcts. (A) Mixed-effects multi-linear regression analysis showed that the normalized permittivity (ratio of electrical permittivity of infarcted sections to remote sections, $\bar{\varepsilon}$) was dependent on [Fe]; (B) however, a similar dependence was not found between normalized conductivity (ratio of electrical conductivity of infarcted sections to remote sections, $\bar{\sigma}$) and [Fe]. (C) Mixed-model linear regression of mean $\bar{\varepsilon}$ measured from Remote, Hemo-, and Hemo+ infarct sections showed significantly greater $\bar{\varepsilon}$ (*, p<0.001) in Hemo+ compared to Remote and Hemo- sections; (D) however, mean $\bar{\sigma}$ measured from Remote, Hemo-, and Hemo+ infarct sections did not show any statistical difference in $\bar{\sigma}$ between the different sections. (E) Mixed-effects multi-linear regression analysis between $\bar{\varepsilon}$ and log(T2*) was found to be dependent on log(T2*); (F) however, a similar dependence was not found between $\bar{\sigma}$ and log(T2*).
Figure 12:
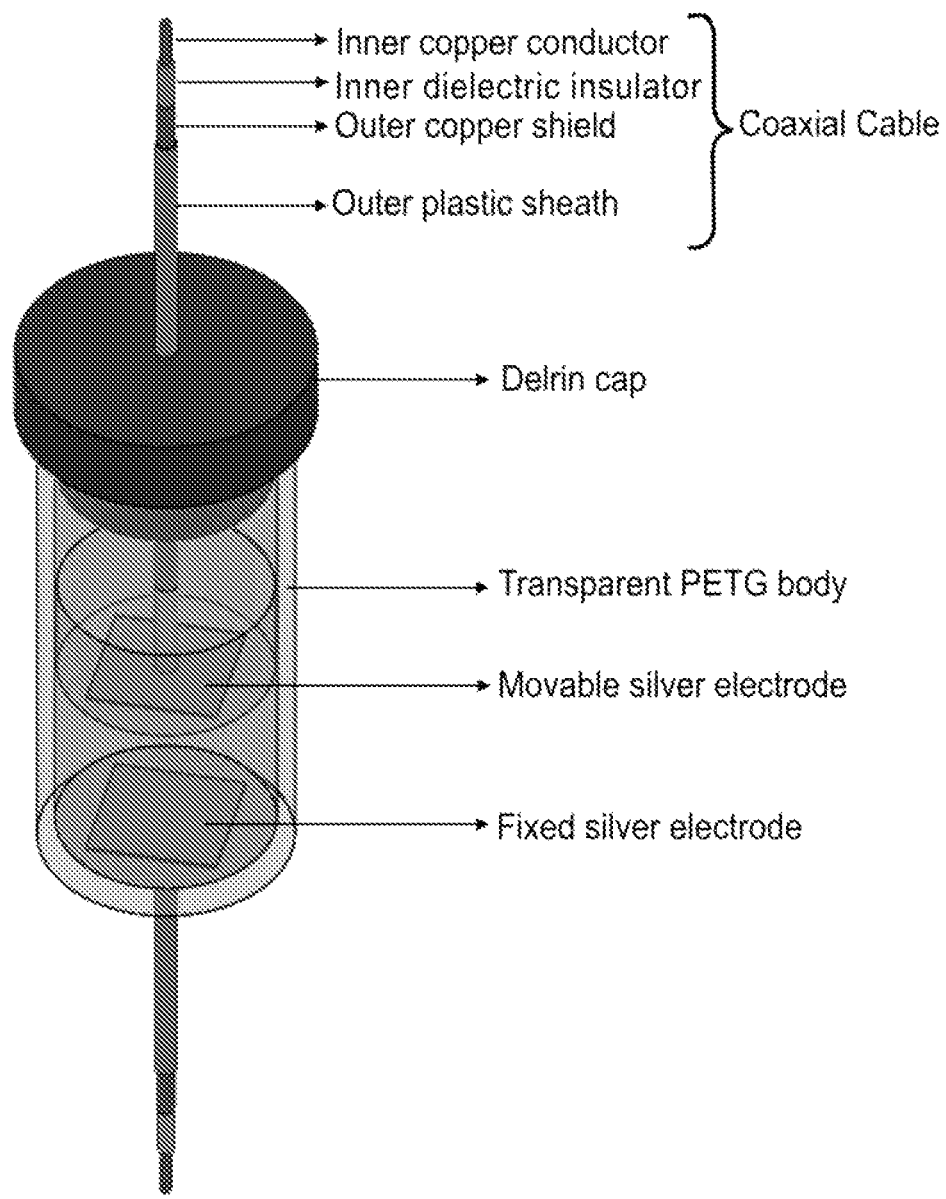
FIG. 12 depicts schematic three-dimensional drawing of a capacitor cell used for tissue electrical measurements.
Figure 14:
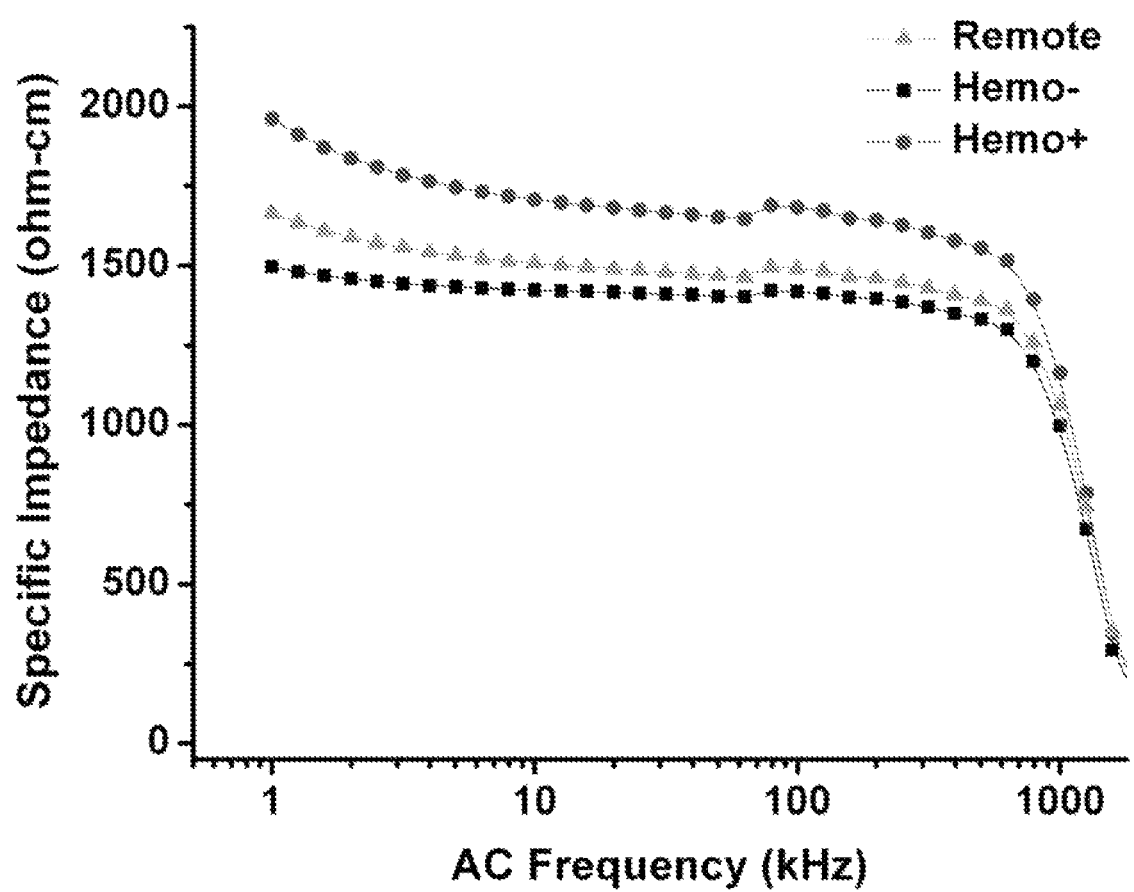
FIG. 14 depicts representative specific impedance spectroscopy measurements from Remote, Hemo−, and Hemo+ myocardial samples. Note that for a given AC frequency, specific impedance of Hemo+ sample is higher than those of the Remote and Hemo− samples.

To investigate the influence of iron deposition on the electrical permittivity and conductivity of infarcted tissue, specific impedance spectra were obtained from ex-vivo tissue samples (Remote, Hemo−, and Hemo+) using a custom-built capacitor cell (FIG. 12) over an alternating-current frequency range of 100 Hz to 10 MHz (FIG. 14). From the impedance measures, estimates of normalized permittivity ($\bar{\varepsilon}$) and conductivity ($\bar{\sigma}$) of Hemo− and Hemo+ tissues (normalized to mean values of remote tissue for the whole-heart), were derived. To mitigate systematic errors in impedance measures from α-dispersion[36] and tissue preparation errors (resulting in unwanted tissue mixing), both of which can be prominent at low frequencies, the analysis was limited to 1 MHz. A mixed-effects multi-linear regression analysis (accounting for variations among animals and tissue slices) was performed to test for the existence of a linear relation between [Fe] (obtained from ICP-MS measurements above) and $\bar{\varepsilon}$ and $\bar{\sigma}$, respectively. Regression analysis showed a statistically significant relation between $\bar{\varepsilon}$ and [Fe]: $\bar{\varepsilon}=1.34$ [Fe]+0.93, with p<0.001; but not between $\bar{\sigma}$ and [Fe], (see FIGS. 6A and 6B). Mean $\bar{\varepsilon}$ for Hemo+ sections was significantly different from mean $\bar{\varepsilon}$ for Hemo− and Remote tissues (p<0.001), while $\bar{\varepsilon}$ of Hemo− and Remote sections were not statistically different from 1 (FIG. 6C). Similarly, comparisons of mean $\bar{\sigma}$ were not significantly different among the different tissue types (FIG. 6D). Averaged across all studies, we observed a mean increase in $\bar{\varepsilon}$ of approximately 25% in the infarcted territories with iron deposition, while no change was observed in remote or infarcted territories without iron. Since the observed changes in $\bar{\varepsilon}$ were not accompanied by changes in $\bar{\sigma}$, it appears that the effect of iron deposition is to transform the infarcted territory into an ideal capacitor.

A noninvasive, image-guided index that can be calibrated against electrical tissue permittivity may be valuable for in-vivo monitoring and characterization of chronically infarcted myocardium. Given that the iron within infarcted tissue influences the myocardial T2* and $\bar{\varepsilon}$ (but not $\bar{\sigma}$) of that tissue, we expected to find a similar relation between T2* and $\bar{\varepsilon}$ (but not $\bar{\sigma}$). A mixed-effects multi-linear regression analysis, performed between log(T2*) and $\bar{\varepsilon}$ and $\bar{\sigma}$, respectively, showed a statistically significant linear relation between $\bar{\varepsilon}$ and log(T2*): $\bar{\varepsilon}=-0.66$ log(T2*)+3.11, with p<0.02; but not between $\bar{\sigma}$ and [Fe], (see FIGS. 6E and 6F). While this analysis showed a strong relation between ex-vivo T2* and $\bar{\varepsilon}$, given the correlation between ex-vivo and in-vivo T2* (FIG. 4B), it is likely that such a relation may also be extended between in-vivo T2* and $\bar{\varepsilon}$. Our findings here showed that it may be possible to acquire a non-invasive marker for changes in electrical permittivity (or capacitance) of infarcted territories with CMR on the basis of T2* relaxometry.

Example 5

Chronic Iron Deposition Takes Place Following Hemorrhagic Myocardial Infarction

A total of 17 canines (3 controls/Shams and 14 subjected to ischemia-reperfusion (I/R) injury (3 hours of ischemia in the territory supplied by the left anterior descending coronary artery (LAD) followed by reperfusion)) were studied. Of the 14 animals with I/R injury, 3 animals were sacrificed on day 3 for gross and histopathologic analysis. The remaining 11 animals were allowed to recover into a chronic phase and sacrificed on day 56, when tissue analysis was performed.

Myocardial tissue analysis from animals sacrificed on day 3 showed that I/R injury led to large myocardial infarctions evidenced by positive staining in TriphenylTetrazolium Chloride (TTC) with internal bleeding at the core of the myocardial infarction. Hematoxylin & Eosin (H&E) stains confirmed the tissue damage and morphological alterations in regions positive for infarction in TTC stainings H&E stains also showed extravasation of RBCs into the interstitial space of the infarcted regions. Perl's stains confirmed a local accumulation of iron in the infarct areas. Gross observation of TTC-stained myocardial tissue from animals with chronic infarcts showed the presence of large infarcted regions with yellowish-brown discoloration at the core of the infarct. H&E stains from the same tissue confirmed the presence of extensive tissue damage and Masson's Trichrome stain showed collagenous tissue in the infarct zone. Interestingly, Perl's stain of corresponding myocardial territories showed a persistent and heterogeneous deposition of iron within the infarction. Iron was also found to be inter-spread among viable cardiomyocytes in incompletely infarcted territories (FIG. 3A (b6), lower inset). For a given stain, tissue from remote (unaffected) territories were similar between acute and chronic stages of the infarction, but were markedly different from infarcted territories (see FIG. 3A).

To examine the extent of iron deposition within chronic infarcts, Inductively Coupled Plasma Mass Spectrometry (ICP-MS) was performed on the myocardial tissue in the chronic stage of shams and animals subjected to I/R injury. Tissue iron content ([Fe], in mg of iron/g of muscle) from Shams, remote (Remote), infarction without hemorrhage (Hemo−), and those with hemorrhagic infarctions (Hemo+) were measured (for further details on the definition/classification of Remote, Hemo−, and Hemo+ tissues, refer to Supplementary Information). The mean value of iron content in Hemo+ was significantly elevated ($p<0.0001$) compared to all the control tissues (Shams, Remote, and Hemo−), (see FIG. 3B). Thus, ICP-MS data shows that hemorrhage from I/R injury leads to nearly an order of magnitude greater iron content in infarcted tissue compared to the different control groups (Shams, Remote, and Hemo−). Our findings are consistent with previous observations of the deposition of iron in tissue in the form of hemosiderin (magnetite-crystalline $Fe_3O_4$ particles) following the biodegradation of RBCs in other pathologies.

Example 6

MRI can Non-Invasively Detect Iron Deposition within Myocardial Infarcts

Biogenic magnetite is known to have the highest conductivity of any cellular material. It is also ferromagnetic in the range of physiological temperatures and acts as a strong dipole in a magnetic field. Magnetic field variations surrounding these "biological bar magnets" can impart significant influence on the phase coherence of protons ($^1H$) and enhance T2* relaxation, which provides opportunities for in-vivo proton Magnetic Resonance Imaging (MRI) (63). To determine if hemosiderin deposition within chronic infarctions can be identified non-invasively, each animal (from above) underwent Cardiovascular Magnetic Resonance (CMR) imaging during the acute (day 3) and chronic (day 56) phase following I/R injury in a whole-body clinical 1.5 T MRI System. Sham-operated animals were imaged at the same time points. Following the in-vivo CMR scan on day 56, animals were sacrificed and the hearts were harvested and imaged. Each scan protocol included the acquisition of myocardial T2* maps for detection of hemorrhage in the acute phase and iron deposition within the infarcted territories in the chronic phase. Late gadolinium enhancement (LE) CMR scans were also performed for detection/confirmation of infarction.

Figure 4:
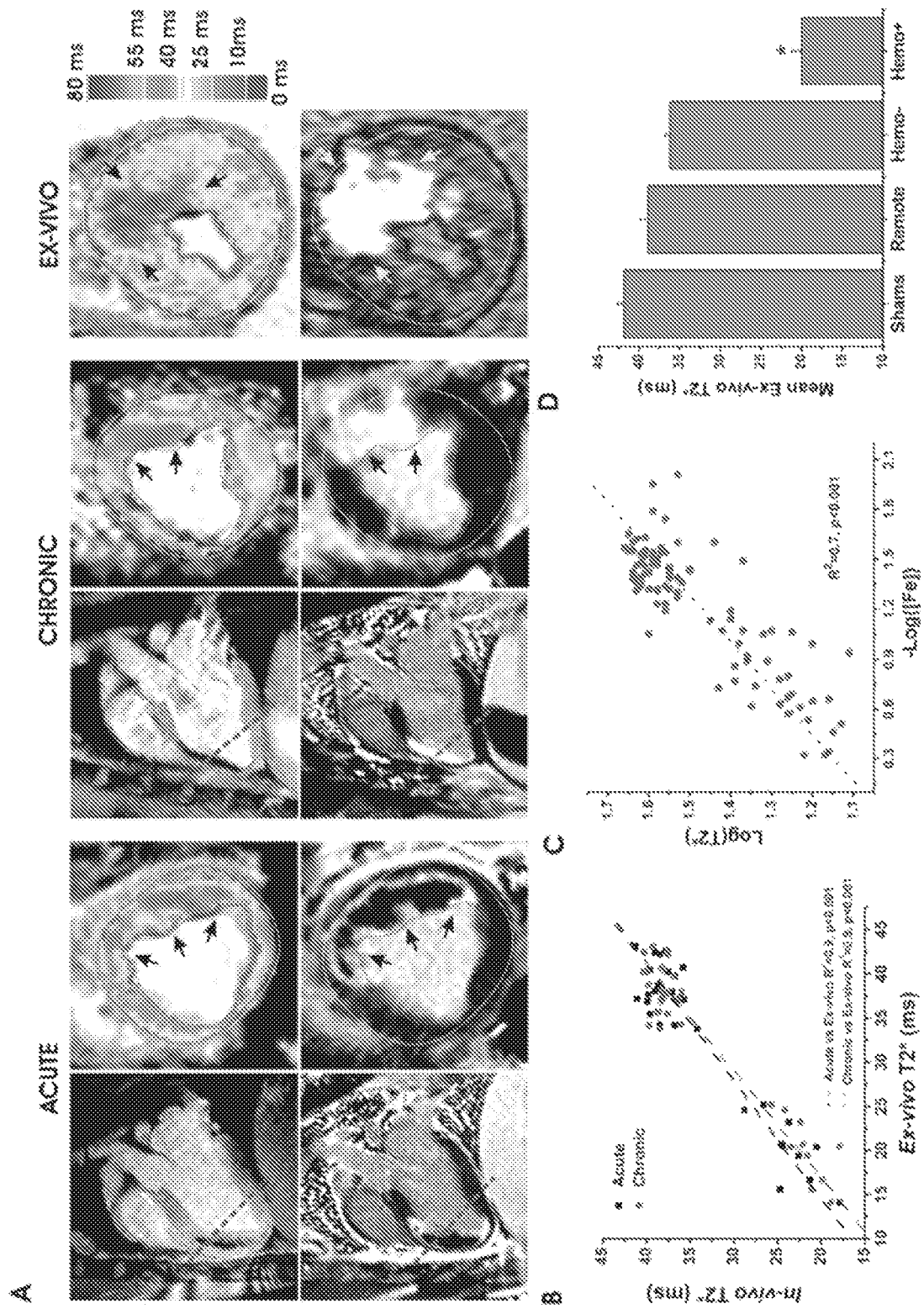
FIG. 4 depicts a Non-invasive CMR image-guided characterization of regional iron deposition following reperfused hemorrhagic myocardial infarction. (A) Representative CMR images (T2* and LE) acquired from an animal with hemorrhagic myocardial infarction in acute and chronic phases along the long- and short-axis (along the dashed red line in the long axis images), along with corresponding ex-vivo images are shown. In-vivo T2* images (both acute and chronic phases) clearly demonstrate the evidence of signal loss in the LAD territory (arrows), where the hemorrhagic infarctions were expected to occur. Arrows in LE images point to the site of infarction. For clarity, T2* maps (color-coded) are provided only along the short axis, and the corresponding long-axis T2*-weighted images, acquired at TE=18 ms, are also shown. (B) Linear regression analysis between in-vivo T2* (acute and chronic) and ex-vivo T2* showed strong correlations indicating that ex-vivo T2* provides a reasonable estimate of in-vivo T2*. (C) Linear regression analysis between ex-vivo log(T2*) and −log([Fe]) showed a strong correlation. (D) Mixed-model linear regression analysis of mean ex-vivo T2* of Shams, Remote, Hemo-, and Hemo+ infarct sections showed significantly lower T2* (*, p<0.001) in Hemo+ compared to all other sections.

Representative images obtained from the CMR studies are shown in FIG. 4A. Significant T2* decreases were observable in the LAD territories (where hemorrhagic infarctions were expected) in the acute and chronic phases. The T2* of Remote and LAD territories in the acute and chronic tissue were nearly constant. From the T2* maps, the mean myocardial T2* values of the sham, Remote, Hemo− and Hemo+ tissues were measured. Pooled mean T2* values from these tissues on days 3 and 56 (in vivo), regressed individually against ex-vivo T2* estimates, showed very strong correlations ($R^2=0.9$ for day 3 vs. ex vivo and 0.9 for day 56 vs. ex vivo; $p<0.001$ for both cases; see FIG. 4B). Regressions between T2* estimates and tissue iron content (determined from ICP-MS) also showed a strong correlation (log(T2*) vs −log([Fe]), $R^2=0.7$; $p<0.001$; see FIG. 4C). Comparison of mean ex-vivo T2* among the different groups showed that only Hemo+ was significantly different from the other groups ($p<0.001$; see FIG. 4D). We also observed that the mean T2* values of Remote, Hemo− and Hemo+ tissues in the acute and chronic tissue to be nearly constant and that the T2* values between Remote and Hemo− tissue groups were not different and were independent on when the T2* measures (acute or chronic) were made. On average, we observed a near 40% decrease in T2* in regions of hemorrhagic infarctions compared to the control groups at 1.5 T. Most notably, the CMR studies showed that iron deposition within chronic hemorrhagic infarctions could be reliably detected and quantified with a whole-body clinical MR scanner.

Example 7

Evidence for Iron Deposition in Humans with Reperfused Myocardial Infarction

The specific long-term consequences of hemorrhagic transformation of myocardial infarction in humans are unknown. We investigated whether patients suspected of having hemorrhagic infarctions showed iron loading within infarcted territories on the basis of CMR. Fifteen patients were enrolled and scanned 3 days and 6 months following successful angioplasty for a first ST-elevation myocardial infarction. Each scan protocol included the acquisition of myocardial T2* maps for detection of hemorrhage in the acute phase and regional iron deposition within the infarcted territories in the chronic phase. Late gadolinium enhancement CMR scans were also prescribed for detection/confirmation of infarction. In the acute phase (day 3), eleven patients were identified positive for having had hemorrhage (T2* decrease within the infarcted myocardium) and four patients were not positive for hemorrhage.

Figure 7:
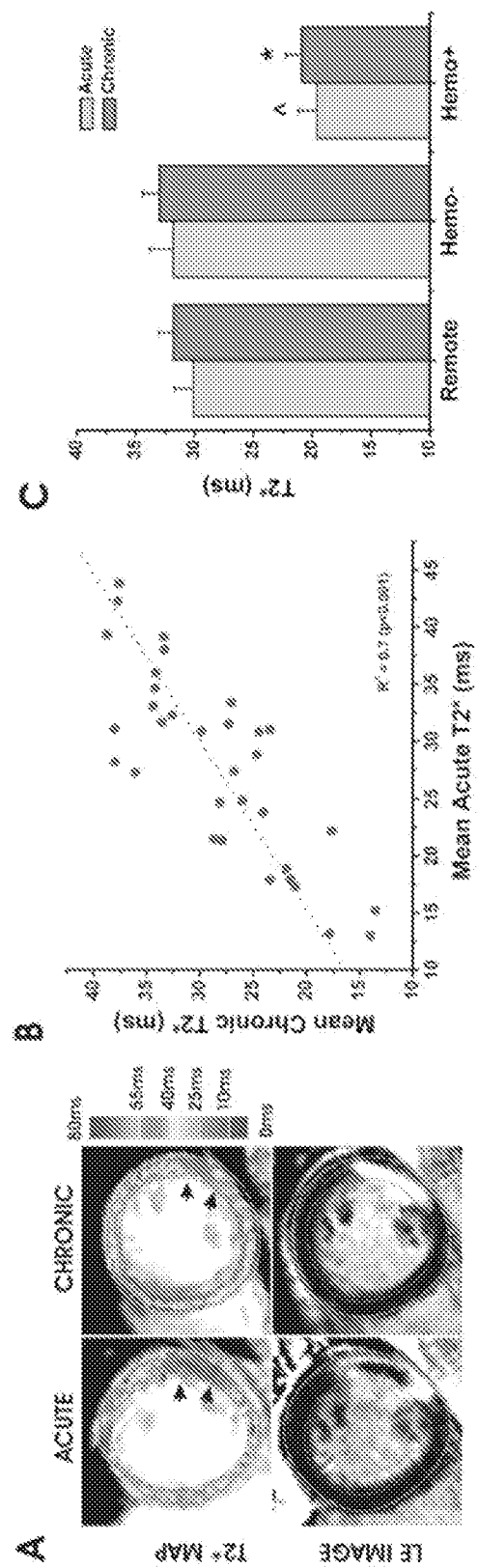
FIG. 7 depicts non-invasive imaging-guided evidence for regional iron deposition in humans following hemorrhagic myocardial infarctions. (A) Representative CMR images (acquired from a 42-year old patient following successful angioplasty) with significant T2* loss (arrows) at the site of acute and chronic myocardial infarction (infarction sites identified by LE imaging, arrows) are shown. (B) Linear regression analysis between acute and chronic T2* showed strong correlations. (C) Mixed-model linear regression analysis of mean T2* of remote, non-hemorrhagic infarct (Hemo-), and hemorrhagic (Hemo+) infarct sections showed significantly lower T2* (^,*, p<0.001) in Hemo+ compared to all other sections in both acute and chronic infarctions, but were not different between remote and Hemo- in both acute and chronic states. However, no differences in T2* were observed between acute and chronic phases in Remote, Hemo-, and Hemo+ tissues.

A representative set of CMR images acquired at 3 days and 6 months post angioplasty in a patient suspected of having had hemorrhagic infarction is shown in FIG. 7A. Significant T2* decreases were observed in the infarcted territories in eleven patients and such losses continued to be evident on the 6-month follow up images. In four patients, T2* losses were not evident on day 3 and were also not detected on the 6-month follow up scans. From the myocardial T2* maps, the mean myocardial T2* values of the Remote, Hemo− and Hemo+ territories were estimated. Pooled mean T2* values from these tissues on day 3 and 6 month, regressed against one-another showed a strong correlation ($R^2=0.70$, $p<0.001$), (see FIG. 7B). Comparison of mean T2* among the different groups obtained from the acute and chronic scans showed that only Hemo+ was significantly different from the other groups ($p<0.001$), (see FIG. 7C).

Consistent with animal studies, we also observed the mean T2* values of Remote, Hemo− and Hemo+ tissues in the acute and chronic tissue to be nearly constant and were similar to T2* values in animals. Moreover, T2* values between Remote and Hemo− tissue groups were not different and were independent on when the T2* measures were made post angioplasty. Similar to the animals studies, on average, we observed an approximate decrease of 40% decrease in T2* in regions of Hemo+ compared to the control sections, Remote and Hemo−. Our findings here indicate that one of the long-term effects of hemorrhage in the chronic stage of infarction is focal loading of iron deposits within the infarcted territories and that such deposits can be detected non-invasively with CMR.

Example 8

Figure 9:
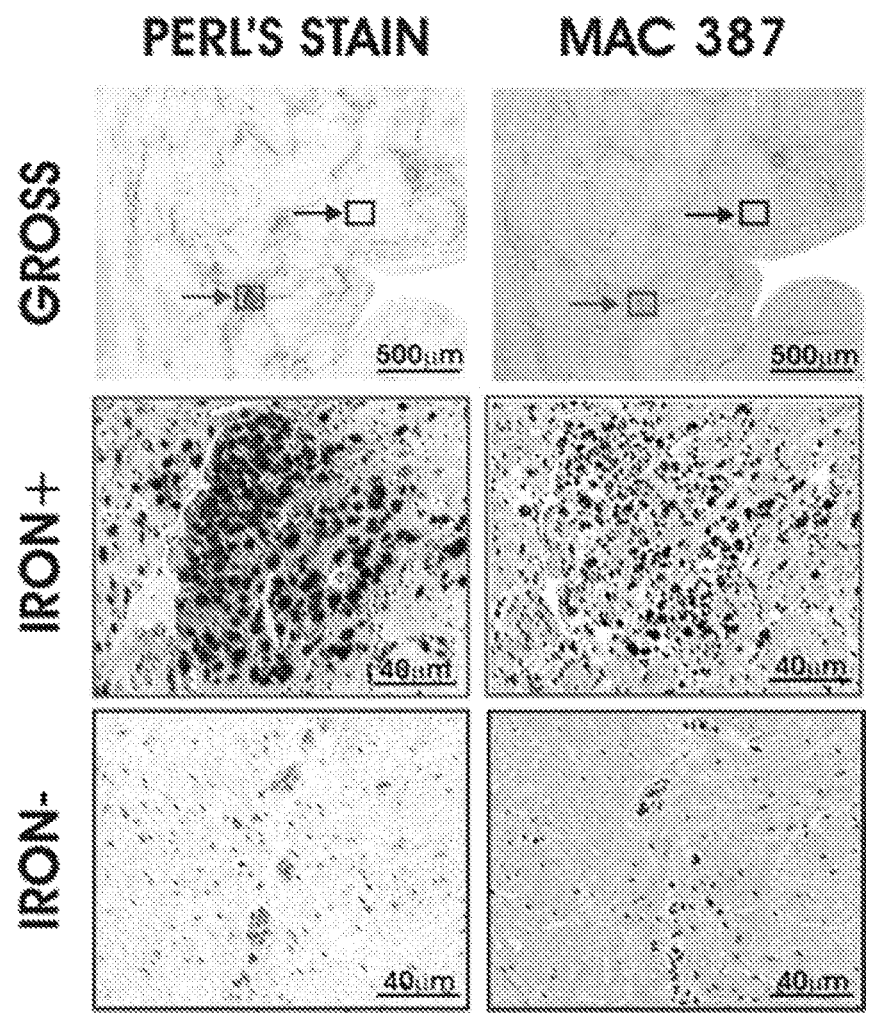
FIG. 9 depicts the co-localization of macrophages with chronic iron deposits. Contiguous histological sections of a chronic hemorrhagic infarction stained with Perl's and MAC 387 stains are shown. Macrophages are highly co-localized with the iron deposits throughout the infarct (GROSS). Magnified regions with (IRON+; red box) and without (IRON−; blue box) iron depositions show that macrophages preferentially co-localize at the site iron depositions.

Evidence for Prolonged Inflammatory Reaction at Sites with Chronic Iron Deposition from Hemorrhagic Myocardial Infarction Tissue sections from animals in Example 6 with and without hemorrhagic infarctions were stained with MAC 387 (for macrophages) stains respectively using standard techniques and imaged at 100× and 400× magnifications. MAC 387 staining of chronic infarctions showed that macrophages were highly co-localized with the chronic iron deposits identified on Perl's stain (FIG. 9). Minimal/no macrophages were observed in the infarcted myocardial territories that were devoid of iron deposits. The long-term deposition of iron, combined with macrophage infiltration at the site of iron, suggests that hemorrhagic infarctions may be subjected to extended periods of inflammation. This may be one of the potential mechanisms associated with adverse cardiac remodeling due to hemorrhagic infarctions.

Example 9

Early Evidence of VT in Dogs with Chronic Hemorrhagic MIs

Figure 8:
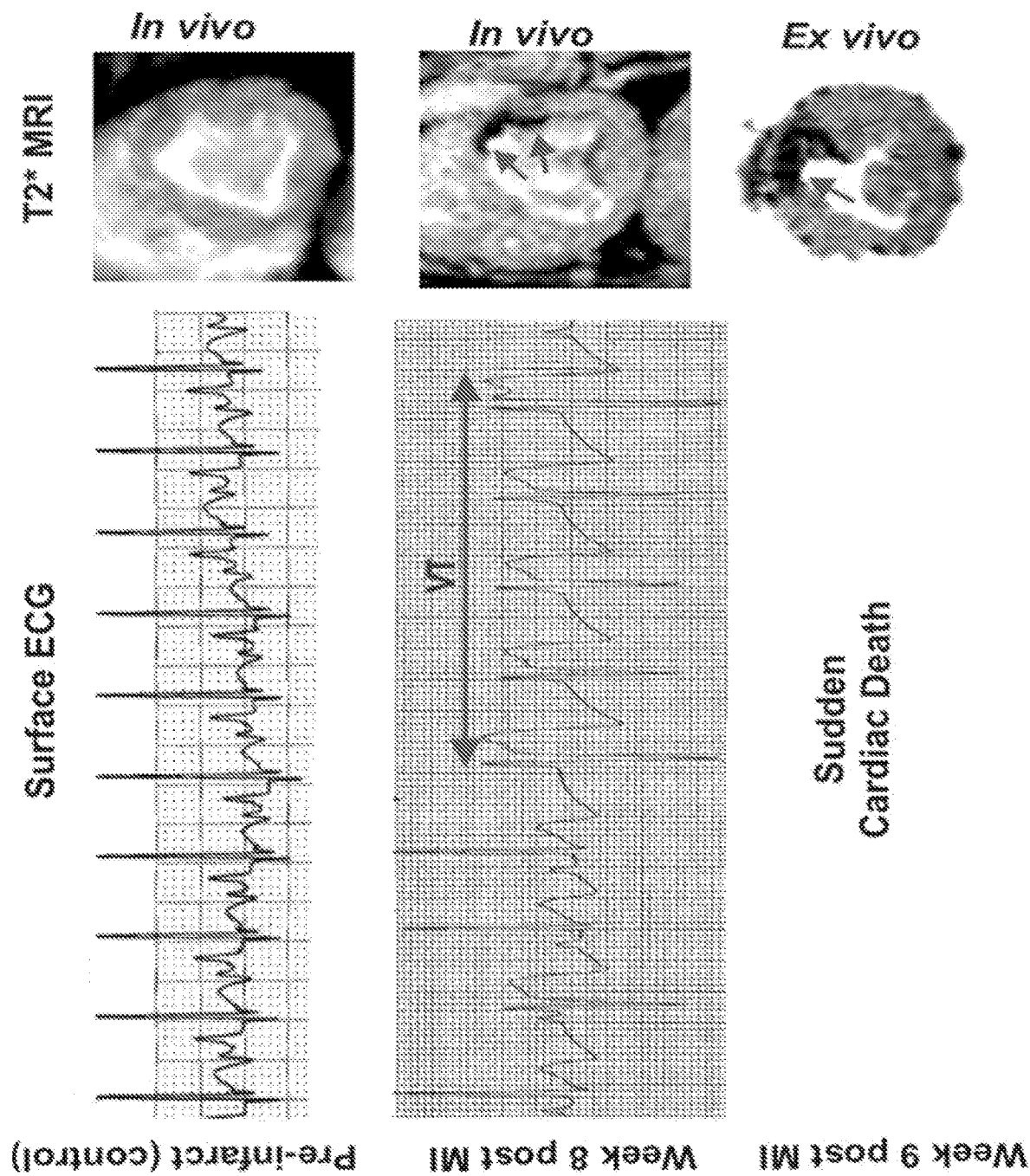
FIG. 8 depicts ECG recordings from a dog with pre- and post-hemorrhagic MI. This figure depicts representative ECG tracings along with T2* MRI from a dog (pre- and post-MI with chronic iron overload) that was succumb to sudden cardiac death (SCD) on week 9 post MI. Ex-vivo T2* MRI, immediately after death, clearly shows the presence of chronic focal iron overload. Note the presence of VT on week 8 (the week preceding SCD). Focal, chronic iron overload in T2* MRI is indicated by arrows (dark cores).

From our studies in Example 5, three animals died from sudden cardiac death before week 10. ECG traces were normal in healthy dogs but pre-mature ventricular complexes (PVCs) were observed in all animals in weeks 8-10 (FIG. 8). Early evidence showing that iron deposition leads to changes in electrical permittivity (Example 4) are significantly increased in regions of chronic MI with iron deposition compared to control tissues. These findings, combined with the evidence of sustained PVCs and VTs, in animals with chronic I/R injury and iron deposits lend further support to the inventor's hypothesis.

Example 10

Evidence for Iron Deposition Following Non-Reperfused Myocardial Infarction

Figure 5:
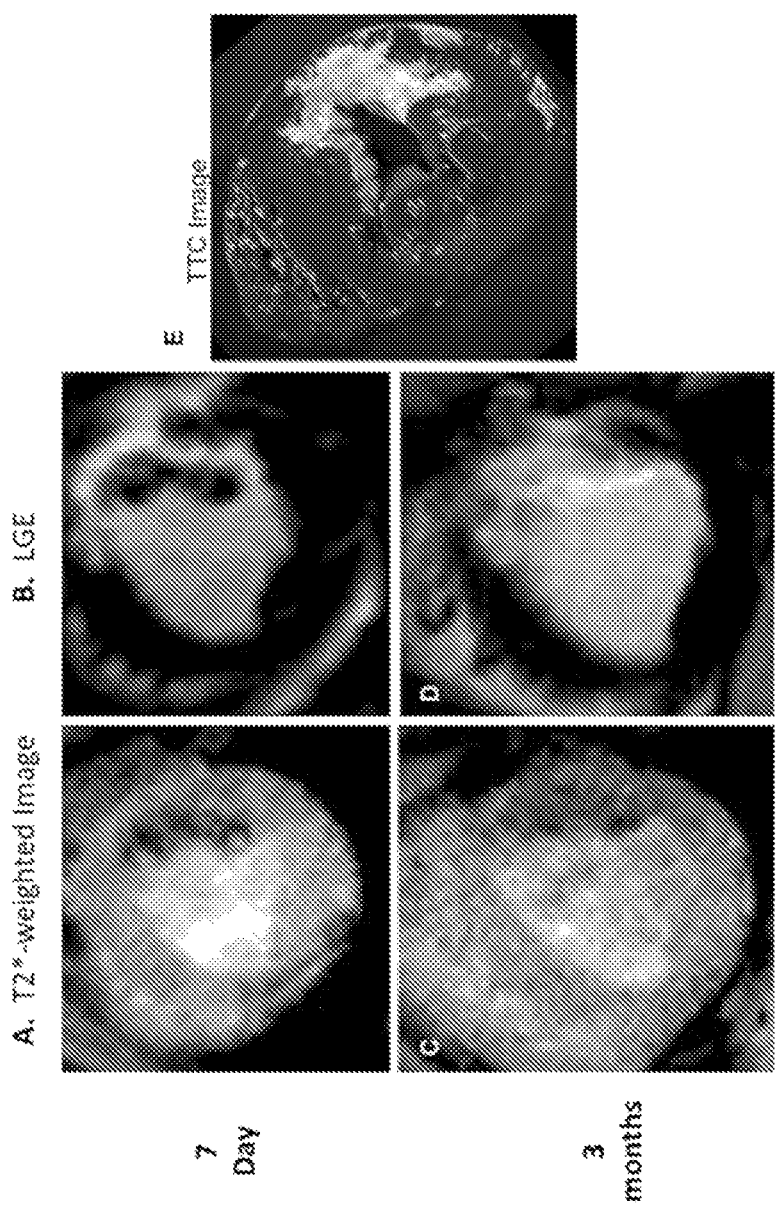
FIG. 5 depicts non-reperfusion hemorrhage mediated iron deposition. This figure depicts an example of short-axis T2* map (A) and DE image (B) from a dog on day 7 post ligation of the left anterior descending coronary artery. As in FIG. 4, T2* changes were more pronounced in regions with hemorrhage. DE MRI showed the area of MI and the extent of microvascular injury (hyperintense core). T2* images of chronic infarction (Day 113 post ligation, C) also show the presence of persistent byproducts of hemorrhage and the DE MR (D) image show region of infarction corresponding to the region with hemorrhage 3 months post MI. (E) The TTC stained image confirms the presence of infarction and the brown discoloration within the infracted territories show presence of iron oxide deposition within the myocardial infarcts.

A total of 16 canines subjected to non-reperfused MI (by permanently ligating left anterior descending coronary artery) were studied. T2* CMR images were acquired on day 7 and 3 months post MI. Images clearly showed the persistence of T2* loss within late enhancement territories on day 7 and week 8. Representative CMR images (on day 7 and month 3) and TTC stained slice acquired from one of the 16 animals is shown in FIG. 5.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method for diagnosing and treating a subject with reperfusion hemorrhage, wherein the subject has had reperfusion therapy following a myocardial infarction (MI), comprising:
obtaining magnetic resonance imaging (MRI) images of the subject's heart; detecting an increase in iron oxide deposition in a hemorrhagic infarcted region of the subject's heart relative to a remote region of the subject's heart from the obtained MRI images; and administering, at least in chronic phase of the MI, an effective amount of a composition comprising a chelating agent, carbon monoxide, a haem-oxygenase regulating drug, or a combination thereof, based on knowledge of an increase in iron oxide deposition in the chronic phase in the infarcted region relative to the remote region following reperfusion hemorrhage, so as to treat the subject and to decrease the risk of sudden cardiac death in the subject.

2. The method of claim 1, further comprising measuring blood levels of any one or more of hepcidin, carbon monoxide, bilirubin, unbound iron binding capacity (UIBC), Fe bound to transferrin, ferritin, heme (heam) oxgenase, biliverdin or a combination thereof, in the subject, wherein an increase in hepcidin biliverdin, bilirubin, carbon monoxide, heme (haem) oxygenase, Fe bound to transferrin, ferritin and/or a decrease in UIBC is indicative of hemorrhagic myocardial infarction in the subject.

3. The method of claim 1, wherein reperfusion hemorrhage in the subject is indicative of increased likelihood of cardiac arrhythmias, and/or adverse cardiac remodeling, and/or heart failure in the subject.

4. The method of claim 3, wherein increased likelihood of cardiac arrhythmias is indicative of increased likelihood of sudden cardiac death in the subject.

5. The method of claim 1, wherein reperfusion hemorrhage in the subject is indicative of a poor prognosis in the subject.

6. The method of claim 1, wherein the subject is a patient with ischemic heart disease.

7. The method of claim 1, wherein the subject is a myocardial infarction patient whose reperfusion therapy was initiated at least 4 hours after the onset of symptoms of myocardial infarction.

8. The method of claim 7, wherein the symptoms of myocardial infarction are any one or more of chest pain, elevated ST segment in an electrocardiogram (ECG) and/or elevated troponin levels in the blood.

9. The method of claim 1, wherein the subject is a human.

10. The method of claim 1, wherein the increase in iron oxide deposition in the hemorrhagic infarcted region of the heart relative to the remote region of the heart results in cardiac arrhythmia, and/or adverse cardiac remodeling, and/or heart failure, and/or sudden cardiac death.

11. The method of claim 3, wherein cardiac arrhythmia is atrial arrhythmia or ventricular arrhythmia.

12. The method of claim 1, wherein the subject has undergone one or more hemorrhagic myocardial infarctions.

13. The method of claim 4, wherein the subject is implanted with an implantable cardioverter-defibrillator (ICD) or a pacemaker.

14. The method of claim 1, wherein the composition comprises an iron chelating agent.

15. The method of claim 14, wherein the iron chelating agent is Deferoxamine, Deferasirox, Deferiprone or a combination thereof.

16. The method of claim 1, wherein the chelating agent, the carbon monoxide and/or the haem-oxygenase regulating drug are administered concurrently or sequentially.

17. The method of claim 1, wherein the MRI images are obtained over a period of time following reperfusion therapy, wherein the period of time is selected from any one or more of 4-24 hours, 1-5 days, 5-10 days, 10-15 days, 15-20 days, 20-25 days 25-30 days, and from 56 days to 6 months.

18. The method of claim 1, wherein the MRI images are obtained during a chronic phase following the reperfusion therapy.

19. The method of claim 1, wherein the Mill images are obtained at a time period between about 56 days following the reperfusion therapy and about 6 months following the reperfusion therapy.

20. The method of claim 1, wherein the MRI images are obtained by free-breathing MRI.

21. The method of claim 1, wherein the administration at least in the chronic phase comprises administering from 10 days to 15 days, from 15 days to 20 days, from 20 days to 25 days, from 25 days to 30 days, or from 56 days to 6 months following the reperfusion therapy.

* * * * *